United States Patent [19]

Miwa et al.

[11] Patent Number: 5,676,142

[45] Date of Patent: Oct. 14, 1997

[54] METHOD AND APPARATUS FOR MEASURING SCATTERING PROPERTY AND ABSORPTION PROPERTY IN SCATTERING MEDIUM

[75] Inventors: Mitsuharu Miwa; Yutaka Tsuchiya; Yukio Ueda, all of Hamamatsu, Japan

[73] Assignee: Hamamatsu Photonics K.K., Hamamatsu, Japan

[21] Appl. No.: 551,746

[22] Filed: Nov. 7, 1995

[30] Foreign Application Priority Data

Nov. 7, 1994 [JP] Japan .................... 6-272508

[51] Int. Cl.[6] .................................... A61B 5/000
[52] U.S. Cl. .......................................... 128/633
[58] Field of Search .................. 128/633, 664–667; 356/39–41

[56] References Cited

U.S. PATENT DOCUMENTS

| | | | |
|---|---|---|---|
| 5,119,815 | 6/1992 | Chance | 128/633 |
| 5,386,827 | 2/1995 | Chance et al. | 128/633 |
| 5,517,987 | 5/1996 | Tsuchiya | 128/633 |
| 5,529,065 | 6/1996 | Tsuchiya | 128/633 |

FOREIGN PATENT DOCUMENTS

| | | |
|---|---|---|
| 0 628 804 | 12/1994 | European Pat. Off. . |
| 0 627 620 | 12/1994 | European Pat. Off. . |
| 2 228 314 | 8/1990 | United Kingdom . |
| 93/13395 | 7/1993 | WIPO . |
| 94/22361 | 10/1994 | WIPO . |

OTHER PUBLICATIONS

Wilson et al, "Optical Reflectance and Transmittance of Tissues: Principles and Applications", IEEE Journal of Quantum Electronics, vol. 26, No. 12, Dec. 1990, New York, pp. 2186–2199.

Sevick et al., "Quantitation of Time–and Frequency–Resolved Optical Spectra for the Determination of Tissue Oxygenation", Analytical Biochemistry, vol. 195, 1991, pp. 330–351.

Patterson et al, "Time Resolved Reflectance and Transmittance for the Non–Invasive Measurement of Tissue Optical Properties", Applied Optics, vol. 28, No. 12, Jun. 15, 1989, pp. 2331–2336.

*Primary Examiner*—Lee S. Cohen
*Assistant Examiner*—Bryan K. Yarnell
*Attorney, Agent, or Firm*—Cushman Darby & Cushman IP Group of Pillsbury Madison & Sutro LLP

[57] ABSTRACT

Measuring scattering and absorption properties of a scattering medium according to the following: (a) causing pulsed measuring light having a predetermined wavelength to enter the scattering medium; (b) performing time-resolved measurement of the measuring light having diffusively propagated in the scattering medium at light detection positions corresponding to a plurality of combinations, each comprising a light incidence position on the scattering medium in the first step and a light detection position on the scattering medium where the measuring light entered the scattering medium in the first step and a light detection position on the scattering medium where the measuring light is detected, having different incidence-detection distances between the light incidence position and the light detection position; (c) calculating a plurality of mean optical pathlengths of the measuring light corresponding to the plurality of incidence-detection distances, based on results of the time-resolved measurement measured in the second step; and (d) calculating a scattering coefficient and an absorption coefficient in the scattering medium, based on a plurality of simultaneous relations consisting of calculation values of the plurality of mean optical pathlengths corresponding to the incidence-detection distances, calculated in the third step, and a theoretical equation of the mean optical pathlengths derived in correspondence to light diffusion properties comprising a scattering property and an absorption property in diffusive propagation paths in the scattering medium.

20 Claims, 10 Drawing Sheets

APPARATUS FOR MEASURING SCATTERING AND ABSORPTION PROPERTIES IN SCATTERING MEDIUM

INCIDENCE OF LIGHT    DETECTION OF LIGHT

SCATTERING MEDIUM B

PROCESS OF LIGHT DIFFUSIVELY PROPAGATING IN SCATTERING MEDIUM

SETTING OF VIRTUAL LIGHT SOURCE TO SCATTERING MEDIUM

SIMULATION RESULT OF TIME-RESOLVED MEASUREMENT BASED ON LIGHT DIFFUSION EQUATION

PRINCIPLE OF MEASURING MEAN OPTICAL PATHLENGTH IN SCATTERING MEDIUM

PRINCIPLE OF MEASURING MEAN OPTICAL PATHLENGTH IN SLAB SCATTERING MEDIUM

NEAR-INFRARED ABSORPTION SPECTRA
OF HEMOGLOBIN (Hb) AND MYOGLOBIN (Mb)

APPARATUS FOR MEASURING SCATTERING AND
ABSORPTION PROPERTIES IN SCATTERING MEDIUM

LIGHT INCIDENCE THROUGH CONDENSER LENS

LIGHT INCIDENCE THROUGH OPTICAL FIBER

LIGHT INCIDENCE THROUGH PINHOLE

LIGHT INCIDENCE THROUGH OPTICAL FIBER INSERTED IN BODY

DIRECT DETECTION OF LIGHT

DETECTION OF LIGHT THROUGH OPTICAL FIBER

DETECTION OF LIGHT THROUGH CONDENSER LENS

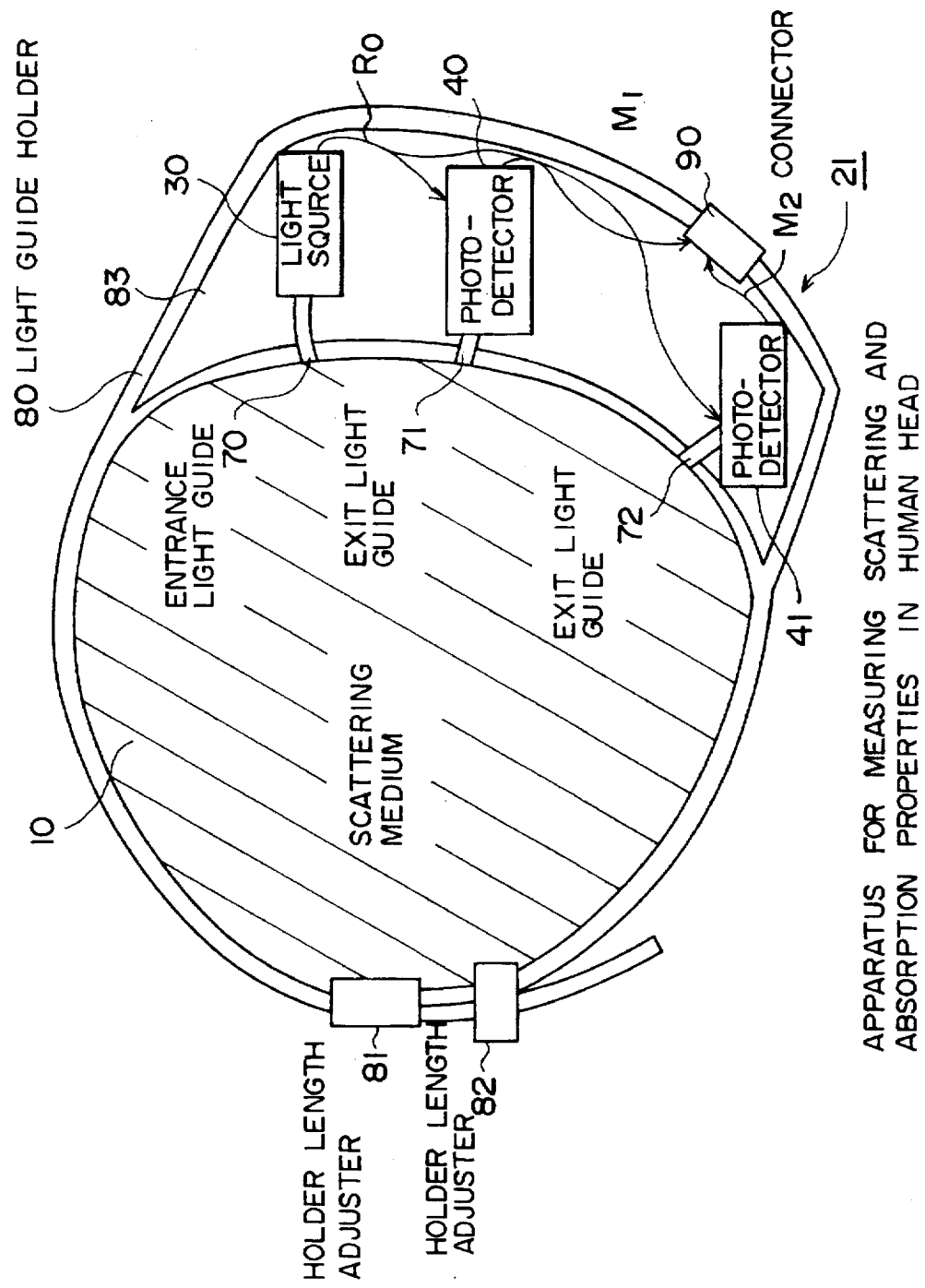

APPARATUS FOR MEASURING SCATTERING AND
ABSORPTION PROPERTIES IN HUMAN MAMMA

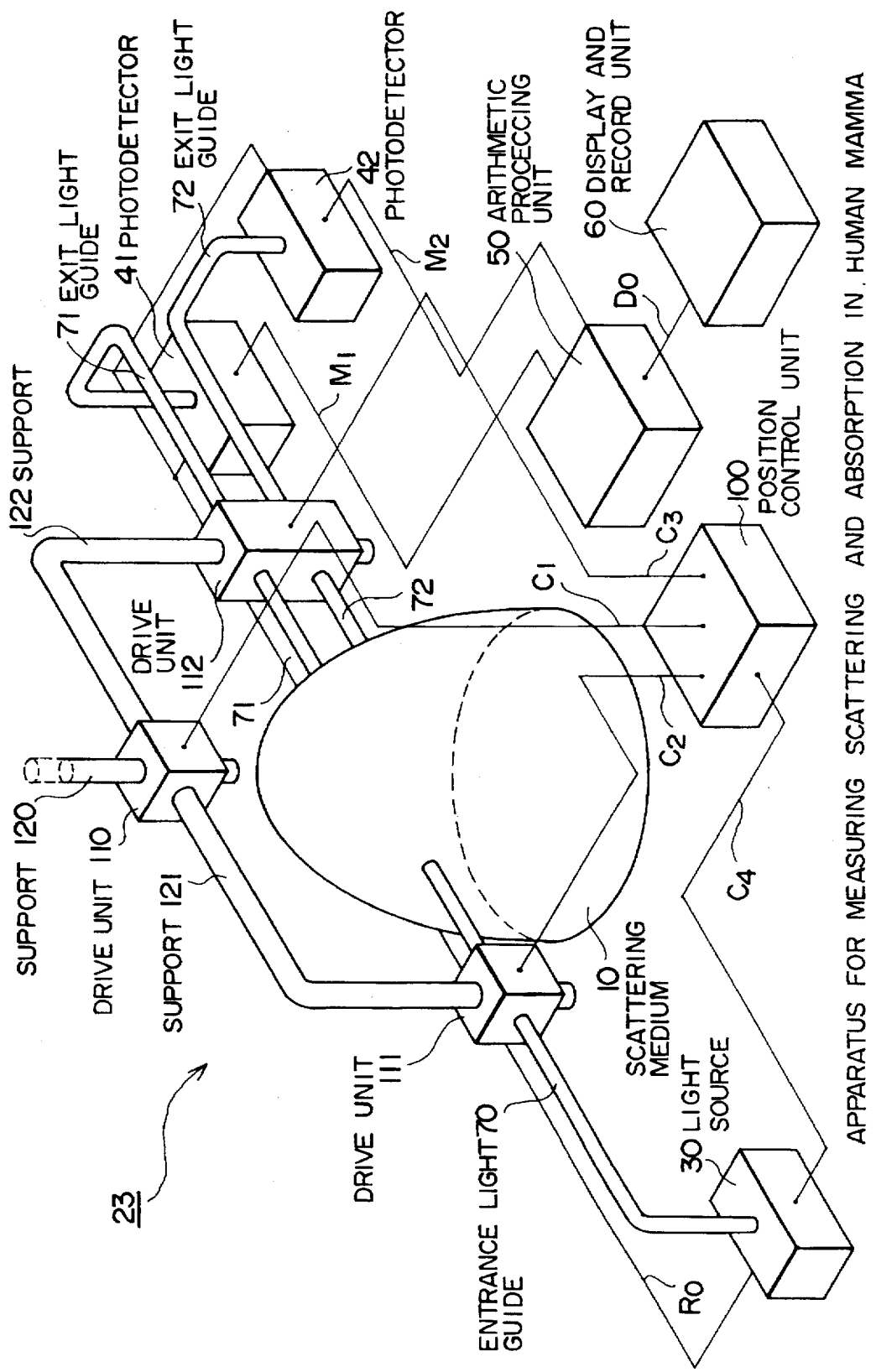

METHOD AND APPARATUS FOR MEASURING SCATTERING PROPERTY AND ABSORPTION PROPERTY IN SCATTERING MEDIUM

BACKGROUND OF THE INVENTION

1. Field of the Invention

The present invention relates to a method and apparatus for measuring a scattering property and an absorption property in a scattering medium, which are used as a non-invasive measuring technique in the fields of medicine, science, etc., which measure a scattering coefficient and an absorption coefficient in a scattering medium (for example, a living tissue), which measure a concentration of an absorptive constituent (for example, hemoglobin) contained in the scattering medium, and which measure temporal changes or spatial distributions of these quantified values.

2. Related Background Art

Examples of the conventional technology for measuring the absorption coefficient and scattering coefficient in the scattering medium are techniques in which continuous or pulsed light as measuring light is let to enter the scattering medium and the measuring light emerging from the scattering medium is measured by time quadrature (integration over time) or time resolution thereof.

In the first technique employing the measurement by time quadrature (time quadrature measurement), an absorbance in the scattering medium is measured based on the basic principle of the so-called Beer-Lambert's law. According to this basic principle, the absorbance in the scattering medium is in a proportional relation with a product among a molar absorption coefficient of an absorptive constituent contained in the scattering medium, a concentration of the absorptive constituent, and an optical pathlength of the measuring light having traveled in the scattering medium. Here, the optical pathlength of the measuring light is given by a physical distance between a light incidence position on the scattering medium where the measuring light is incident and a light detection position on the scattering medium where the measuring light is detected.

In the second technique employing the measurement by time resolution (time-resolved measurement), the absorption coefficient in the scattering medium is measured based on waveform analysis of the measuring light with expanded pulse width in the scattering medium. According to the waveform analysis, the absorption coefficient in the scattering medium is coincident with a time-differentiated value of light intensity of the measuring light after a sufficient time has elapsed from incidence of the measuring light. Here, the sufficient time, which has elapsed from incidence of the measuring light, is given by a time when the light intensity of the measuring light is sufficiently attenuated. Information concerning the above prior art is described in detail, for example, in a reference, "Applied Optics, vol. 28, no. 12, pp. 2331–2336, 1989."

SUMMARY OF THE INVENTION

In the above conventional technique performing the time quadrature measurement, a measured value of the absorbance in the scattering medium includes an error due to such approximation that the optical pathlength of the measuring light changing depending upon the both scattering coefficient and absorption coefficient in the scattering medium is constant. In the above conventional technology performing the time-resolved measurement, a measured value of an absorption coefficient in the scattering medium includes an error due to measurement of a signal component in a weak measuring light at considerably degraded signal-to-noise (S/N) ratios.

Therefore, an object of the present invention is to provide a method and apparatus for measuring a scattering property and an absorption property in the scattering medium, which can improve measurement accuracy by reducing the measurement errors, based on theoretically and experimentally sufficient analysis on a process of the light diffusively propagating in the scattering medium.

In order to achieve the above object, a method for measuring a scattering property and an absorption property in a scattering medium according to the present invention comprises: (a) a first step of letting pulsed measuring light having a predetermined wavelength enter a scattering medium; (b) a second step of performing time-resolved measurement of the measuring light having diffusively propagated in the scattering medium at light detection positions corresponding to a plurality of combinations, each comprised of a light incidence position on the scattering medium where the measuring light was let to enter the scattering medium in the first step and a light detection position on the scattering medium where the measuring light is detected, having different incidence-detection distances between the light incidence position and the light detection position; (c) a third step of calculating a plurality of mean optical pathlengths of the measuring light corresponding to the plurality of incidence-detection distances, based on results of the time-resolved measurement measured in the second step; and (d) a fourth step of calculating a scattering coefficient and absorption coefficient in the scattering medium, based on a plurality of simultaneous relations consisting of calculation values of the plurality of mean optical pathlengths corresponding to the plurality of incidence-detection distances, calculated in the third step, and a theoretical equation of the mean optical pathlength derived in correspondence to light diffusion properties comprising a scattering property and an absorption property in diffusive propagation paths in the scattering medium.

The first step comprises setting a plurality of wavelengths having different absorption coefficients for absorptive constituents in the scattering medium and exceeding a number of types of the absorptive constituents, for the measuring light, the second step comprises performing time-resolved measurement of the measuring light for the plurality of wavelengths exceeding the number of types of absorptive constituents, the third step comprises calculating the plurality of mean optical pathlengths of the measuring light for the plurality of wavelengths exceeding the number of types of the absorptive constituents, and the fourth step comprises calculating the plurality of absorption coefficients in the scattering medium for the plurality of wavelengths exceeding the number of types of the absorptive constituents; and the method may further comprise a fifth step of calculating concentrations of the absorptive constituents, based on a plurality of simultaneous relations consisting of the plurality of calculation values of the absorption coefficients in the scattering medium for the plurality of wavelengths exceeding the number of types of the absorptive constituents, calculated in the fourth step, and a theoretical equation of the absorption coefficient derived in correspondence to light attenuation properties including contribution of the absorptive constituents in diffusive propagation paths inside the scattering medium.

In order to achieve the above object, an apparatus for measuring a scattering property and an absorption property in a scattering medium according to the present invention comprises: (a) a light source for generating pulsed measuring light having a predetermined wavelength; (b) an entrance light guide for outputting the measuring light coming from the light source into a scattering medium; (c) a photodetector for performing time-resolved measurement of the measuring light having diffusively propagated in the scattering medium at light detection positions corresponding to a plurality of combinations, each comprised of a light incidence position on the scattering medium where the measuring light was made incident thereinto by the light guide and a light detection position on the scattering medium where the measuring light is detected, having different incidence-detection distances between the light incidence position and the light detection position; (d) an optical pathlength arithmetic unit for calculating a plurality of mean optical pathlengths of the measuring light corresponding to the plurality of incidence-detection distances, based on results of the time-resolved measurement measured by the photodetector; and (e) a light diffusion arithmetic unit for calculating a scattering coefficient and an absorption coefficient in the scattering medium, based on a plurality of simultaneous relations consisting of calculation values of the plurality of mean optical pathlengths corresponding to the plurality of incidence-detection distances, calculated in the optical pathlength arithmetic unit, and a theoretical equation of the mean optical pathlength derived in correspondence to light diffusion properties comprising a scattering property and an absorption property in diffusive propagation paths inside the scattering medium.

The light source has wavelength controlling means for setting a plurality of wavelengths having different absorption coefficients for absorptive constituents in the scattering medium and exceeding a number of types of the absorptive constituents, for the measuring light, the photodetector performs time-resolved measurement of the measuring light for the plurality of wavelengths exceeding the number of types of absorptive constituents, the optical pathlength arithmetic unit calculates the plurality of mean optical pathlengths of the measuring light for the plurality of wavelengths exceeding the number of types of the absorptive constituents, and the light diffusion arithmetic unit calculates the plurality of absorption coefficients in the scattering medium for the plurality of wavelengths exceeding the number of types of the absorptive constituents; and the apparatus may further comprise a light absorption arithmetic unit for calculating concentrations of the absorptive constituents, based on a plurality of simultaneous relations consisting of the plurality of calculation values of the absorption coefficients in the scattering medium for the plurality of wavelengths exceeding the number of types of the absorptive constituents, calculated in the light diffusion arithmetic unit, and a theoretical equation of the absorption coefficient derived in correspondence to light attenuation properties including contribution of the absorptive constituents in diffusive propagation paths inside the scattering medium.

In the method and apparatus for measuring the scattering property and absorption property in the scattering medium according to the present invention, arranged as described above, the pulsed measuring light having diffusively propagated inside the scattering medium as affected by scattering and absorption is measured in a non-invasive manner outside the scattering medium, and the scattering property and absorption property in the scattering medium are calculated by arithmetic processing of the measurement results. On this occasion, utilizing the fact that the mean optical pathlength of the measuring light depends upon the light diffusion properties including the scattering property and absorption property in the diffusive propagation paths inside the scattering medium, measurement is carried out for the scattering coefficient and absorption coefficient in the scattering medium, based on the mean optical pathlengths measured for two or more different incidence-detection distances between light incidence position and light detection position.

Here, if the scattering light is set to have different wavelengths having different absorption coefficients for absorptive constituents contained in the scattering medium and selected in a number not less than a number of types of the absorptive constituents, measurement of concentrations of the absorptive constituents can be performed based on absorption coefficients measured for the different wavelengths, utilizing the fact that the absorption coefficients in the scattering medium for the respective wavelengths depend upon light attenuation properties including contribution of the respective absorptive constituents in the diffusive propagation paths inside the scattering medium.

If such measurement is carried out at the same light incidence position and light detection position but at different times, time changes of those quantified values can be measured. Further, if such measurement is carried out as changing the light incidence position and light detection position, spatial distributions of those quantified values can be measured.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 10 is a sectional view to diagrammatically show the major part of an apparatus for measuring the scattering property and absorption property in a human head;

FIG. 12 is a perspective view to diagrammatically show an apparatus for measuring the scattering property and absorption property in a human mamma and imaging them.

DESCRIPTION OF THE PREFERRED EMBODIMENTS

Figure 1:
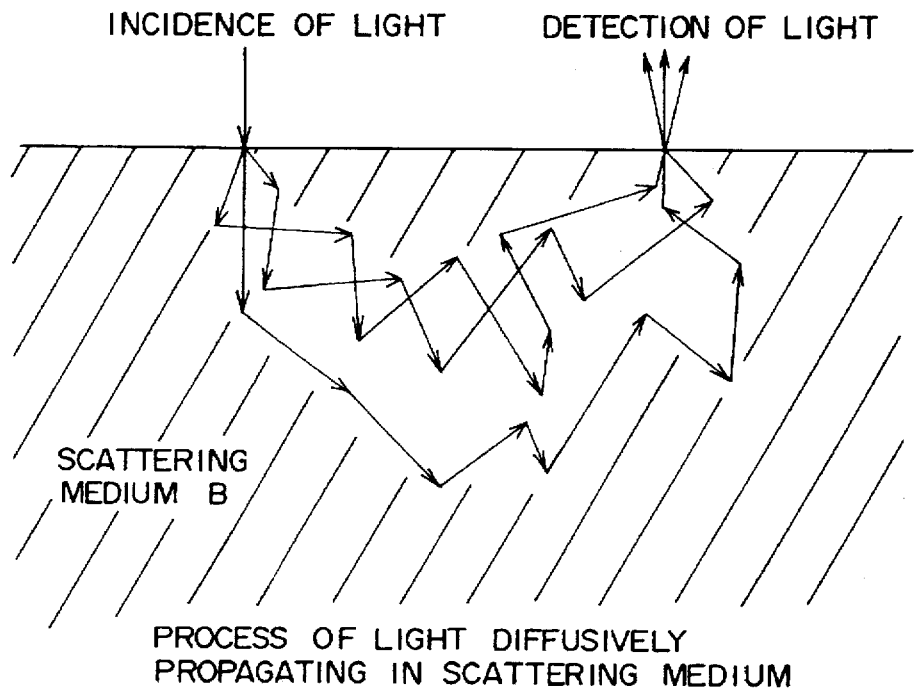
FIG. 1 is a sectional view to diagrammatically show a process in which light is diffusively propagating in a scattering medium.

The constitution and operation of embodiments of the method and apparatus for measuring the scattering property and absorption property in the scattering medium according to the present invention will be explained in detail with reference to FIG. 1 to FIG. 12. In the description with the drawings, same elements will be denoted by same reference numerals and redundant explanation will be omitted.

(1) Method for measuring scattering property and absorption property in scattering medium (1.1) Measurement principle of scattering coefficient and absorption coefficient As shown in FIG. 1, light entering the interior of the scattering medium B is subject to scattering and absorption, thus diffusively propagates as being attenuated in the scattering medium, and then emerges from the interior of the scattering medium B. Namely, the light travels in a zigzag path, because it is scattered at random by scattering constituents. On the other hand, because the light is gradually absorbed by absorptive constituents, a quantity of light exponentially is attenuated according to a traveling distance. Although the light is diffused to the almost entire region of the scattering medium B by random scattering, FIG. 1 diagrammatically shows only tracks of photons detected at a light detection position different from a light incidence position on the scattering medium B, i.e., tracks of photons utilized in actual measurement.

It is well known that the process for the light to diffusively propagate in the scattering medium can be precisely described and analyzed based on the photon diffusion theory. According to the photon diffusion theory, pulsed measuring light entering the scattering medium expands the pulse width thereof while diffusively propagating as scattered and absorbed. Information concerning the photon diffusion theory is described in detail, for example, in a reference, "Medical Physics, vol. 19, no. 14, pp. 879–888, 1992."

On the other hand, behavior of individual photons diffusively propagating in the scattering medium is analyzed by computer simulation based on the Monte Carlo method. Experiments are also conducted actually using samples such as physical models of the scattering medium or living samples.

Recent information confirmed good agreement among results of analysis derived from the photon diffusion theory, simulation results by the Monte Carlo method, and experiment results with samples. Thus, it can be considered that the behavior of light diffusively propagating in the scattering medium can be fully accurately described based on the photon diffusion theory.

Based on the photon diffusion theory, a photon diffusion equation in the scattering medium is expressed by Eq. (1) for photon fluence rate $\Phi(r, t)$ and photon generation rate $S(r, t)$ at position r and time t.

$$\frac{1}{c} \frac{\partial}{\partial t} \phi(r,t) - D\nabla^2\phi(r,t) + \mu_A\phi(r,t) = S(r,t) \tag{1}$$

In the above equation, $\Phi(r, t)$: the photon fluence rate [number of photons·mm$^{-2}$·sec$^{-1}$], D: a light diffusion coefficient [mm], $\mu_A$: an absorption coefficient [mm$^{-1}$], c: a light velocity [mm·sec$^{-1}$], $S(r, t)$: a photon generation rate [number of photons·mm$^{-3}$·sec$^{-1}$].

The light velocity c is determined in accordance with the refractive index in the scattering medium.

Here, because the photon generation rate of an impulse light source can be expressed by a delta function, it is given as follows.

$$S(r,t)=\delta(r,t) \tag{2}$$

Thus, light incident from the impulse light source into the scattering medium at the origin (r=0) and at the initial time (t=0) is expressed by Eq. (3) from Eq. (2).

$$S(0,0)=\delta(0,0)=\delta(0)\delta(0) \tag{3}$$

Accordingly, the photon diffusion equation for incidence of impulse light is described by Eq. (4) from Eqs. (1), (3).

$$\frac{1}{c} \frac{\partial}{\partial t} \phi(r,t) - D\nabla^2\phi(r,t) + \mu_A\phi(r,t) = \delta(O)\delta(O) \tag{4}$$

Further, there are relations represented by Eqs. (5), (6) among the various optical constants used in Eq. (4).

$$D=\{3(\mu_A+\mu_{TS})\}^{-1} \tag{5}$$

$$\mu_{TS}=(1-g)\mu_S \tag{6}$$

In the above equations, $\mu_S$: the scattering coefficient [mm$^{-1}$], $\mu_{TS}$: a transport scattering coefficient [mm$^{-1}$], g: a mean cosine of scattering angle θ.

For ordinary living samples, the diffusion constant can be approximated to $D=(3\mu_{TS})^{-1}$, because the transport scattering coefficient $\mu_{TS}$ is some ten times greater than the absorption coefficient $\mu_A$. There is another theory that the light diffusion coefficient D excludes the absorption coefficient $\mu_A$. In any event, the present invention can be applied to the both theories.

Figure 2:
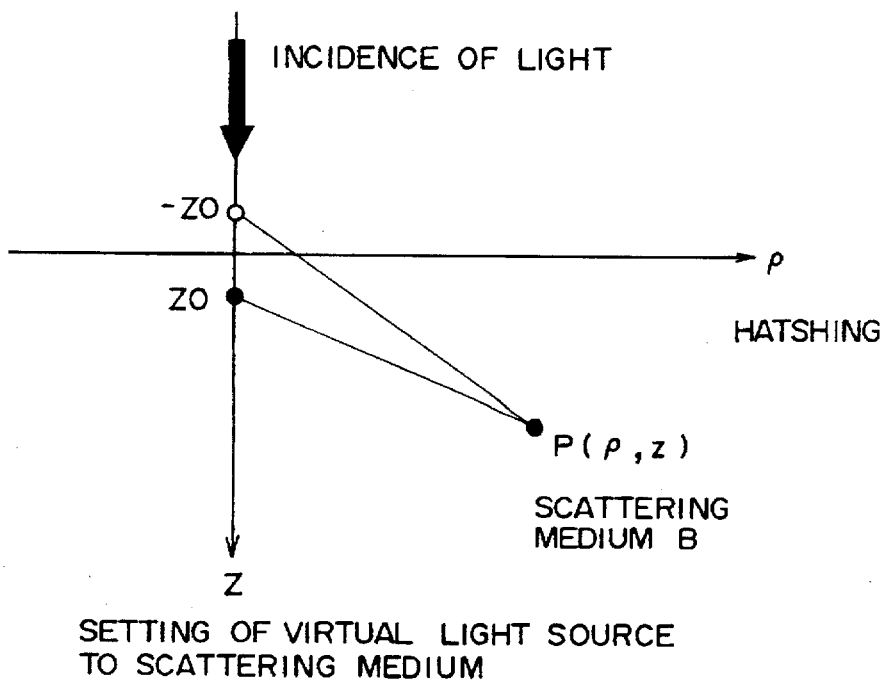
FIG. 2 is a sectional view to diagrammatically show a virtual light source set to realize boundary conditions of a scattering medium for a photon diffusion equation.

Let us assume that spot pulsed light is let to enter the scattering medium B occupying a half space, as shown in FIG. 2. In that case, boundary conditions for the photon diffusion equation represented by Eq. (4) are realized by placing a point light source of the negative polarity at a position ($\rho=0$, $z=-z_0$), using the $\rho$ coordinate axis located along the surface of the scattering medium B and the z coordinate axis located as a normal line to the surface of the scattering medium B. Normal $z_0$ is suitably set to about the reciprocal of the transport scattering coefficient $\mu_{TS}$, but strictly speaking, it changes depending upon a method of incidence of light or properties of scattering constituents contained in the scattering medium B. The reciprocal $\mu_{TS}^{-1}$ of the transport scattering coefficient corresponds to a distance which the light can travel without being affected by scattering, that is, to a mean free path or mean diffusion length.

Based on the above boundary conditions, a solution of the photon diffusion equation shown in Eq. (4) is obtained as a light intensity I ($\rho$, 0, t) [number of photons·mm$^{-2}$·sec$^{-1}$] at an arbitrary position ($\rho$, 0) on the surface of the scattering medium B and at time t, as shown in Eq. (7).

$$I(\rho,0,t) = (4\pi Dc)^{-3/2} t^{-5/2} \exp(-\mu_A ct) \times z_0 \exp\left[ -\frac{z_0^2 + \rho^2}{4Dct} \right] \quad (7)$$

On the other hand, photons incident from the impulse light source into the scattering medium B at the origin ($\rho$=0) and at the beginning (t=0) diffusively propagate in the interior of the scattering medium B as being affected by scattering and absorption. In this case, a mean optical pathlength <L> of photons emerging from the scattering medium and detected is defined as indicated by Eq. (8).

$$\langle L \rangle = \frac{c \int_0^\infty I(\rho,t) t \, dt}{\int_0^\infty I(\rho,t) \, dt} \quad (8)$$

Information concerning the mean optical pathlength is described in detail, for example, in a reference, "Phys. Med. Biol., vol. 37, no. 7, pp. 1531–1560, 1992."

Figure 3:
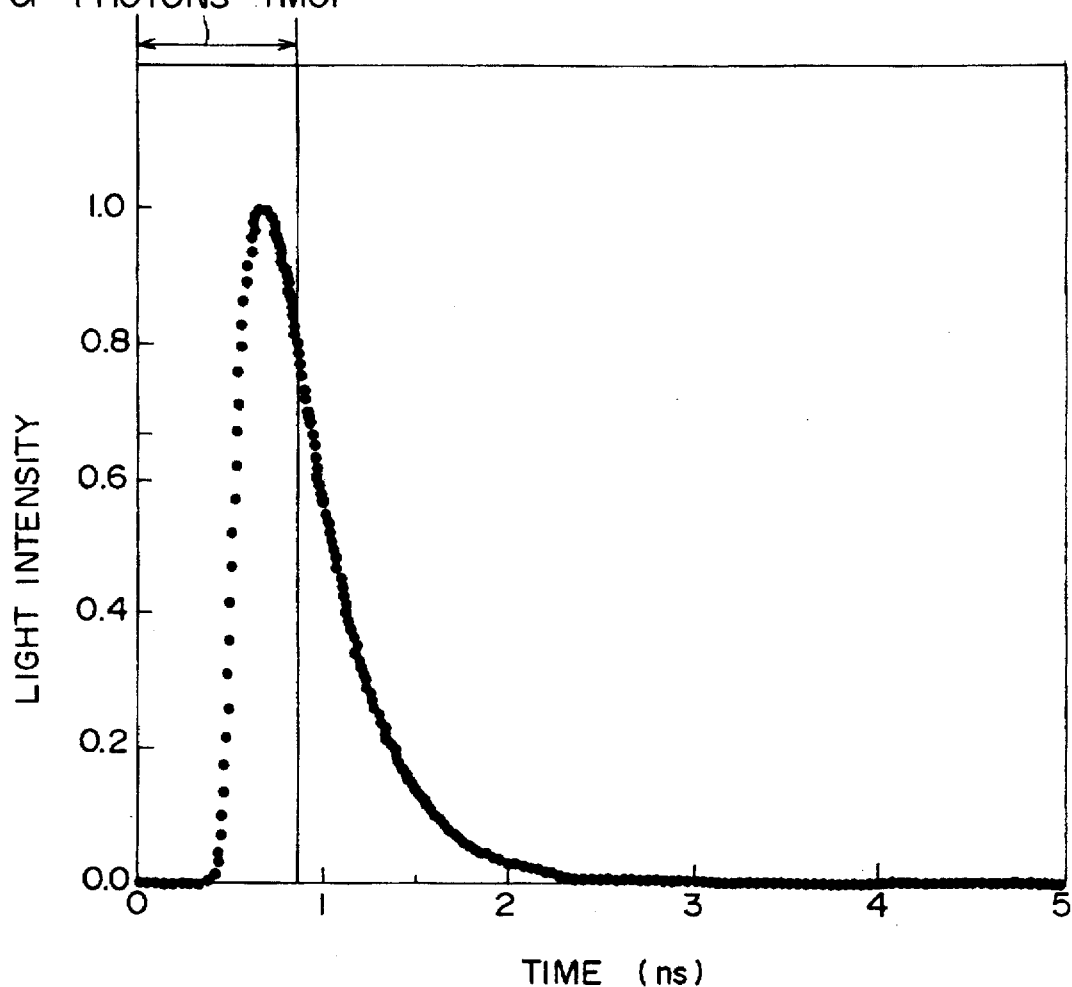
FIG. 3 is a graph to show a simulation result of a mean optical pathlength by time-resolved measurement based on a solution of the photon diffusion equation.

As shown in FIG. 3, when the simulation result assuming the time-resolved measurement is plotted by setting the various optical constants in Eq. (7) as D=0.144 mm, $\mu_A$=0.01 mm$^{-1}$, c=2.2×10$^{11}$ m·sec$^{-1}$, and $\mu_{TS}$=2.3 mm$^{-1}$, the diffusive propagation time $t_{MOP}$ of photon corresponding to the mean optical pathlength calculated by Eq. (8) is positioned as to pass the barycenter of a waveform indicating a temporal change of light intensity.

Here, substituting Eq. (7) into Eq. (8), the mean optical pathlength <L> of photon as to incidence of impulse light is obtained as represented by Eq. (9), based on a distance $\rho$ between the light incidence position and the light detection position (which will be referred to as an incidence-detection distance). Here, $z_E$=2D=2/[3($\mu_A$+$\mu_{TS}$)].

$$\langle L(\rho) \rangle = \frac{1}{Z_E} \cdot \frac{\rho^2 + 4Z_E^2}{1 + \sqrt{\rho^2 + Z_E^2} \sqrt{2\mu_A/Z_E}} \quad (9)$$

The mean optical pathlength <L ($\rho$)> represented by this Eq. (9) is expressed by one known that can be controlled or set, the incidence-detection distance $\rho$, and two unknowns to be measured, the absorption coefficient $\mu_A$ and the transport scattering coefficient $\mu_{TS}$. Therefore, if the incidence-detection distance $\rho$ is controlled or set to two or more different values and if two or more mean optical pathlengths <L ($\rho$)> are calculated by Eq. (8) based on the time-resolved measurement of light intensity, the absorption coefficient $\mu_A$ and transport scattering coefficient $\mu_{TS}$ can be calculated based on simultaneous relations consisting of two or more Equations (9).

Figure 4:
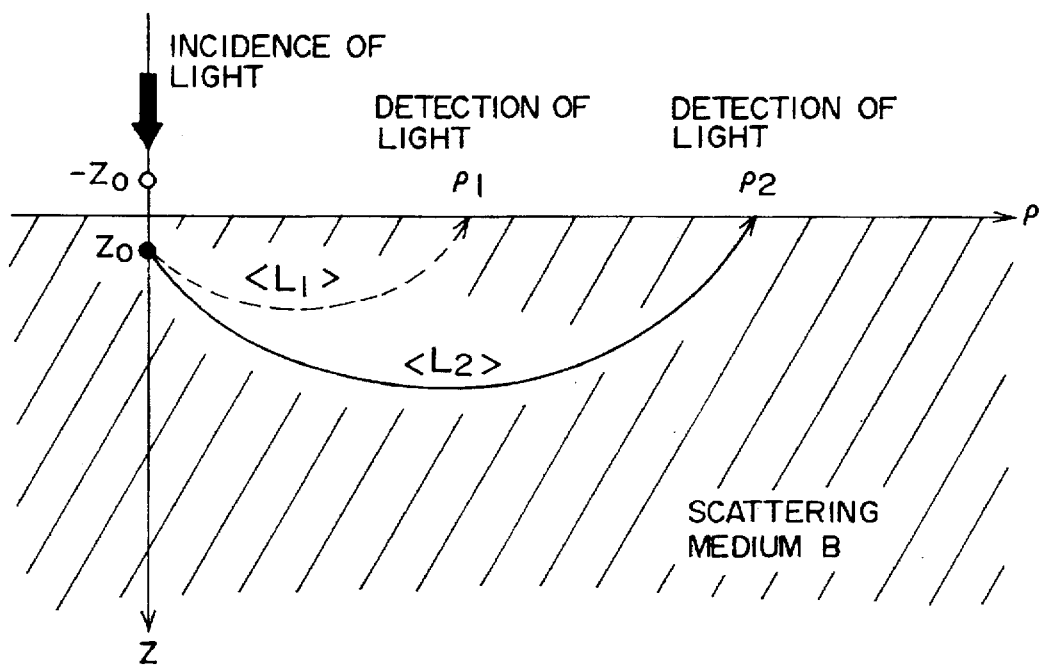
FIG. 4 is a sectional view to diagrammatically show a principle of measuring a mean optical pathlength in a semi-infinite scattering medium.

More specifically, as shown in FIG. 4, pulsed measuring light with a predetermined wavelength at the origin ($\rho$=0) and at the beginning (t=0) is made incident into a scattering medium in which scattering and absorptive constituents are uniformly distributed. Subsequently, the time-resolved measurement of measuring light is carried out at two different incidence-detection distances $\rho_1$, $\rho_2$. Then, based on the two results of the time-resolved measurement, two mean optical pathlengths <L ($\rho_1$)>, <L ($\rho_2$)> are calculated by Eq. 8. Then substituting a combination of the incidence-detection distance $\rho_1$ and mean optical pathlength <L ($\rho_1$)> and a combination of the incidence-detection distance $\rho_2$ and mean optical pathlength <L($\rho_2$)> each into Eq. (9) the following simultaneous relations of Eqs. (10), (11) can be obtained.

$$\langle L(\rho_1) \rangle = \frac{1}{Z_E} \cdot \frac{\rho_1^2 + 4Z_E^2}{1 + \sqrt{\rho_1^2 + Z_E^2} \sqrt{2\mu_A/Z_E}} \quad (10)$$

$$\langle L(\rho_2) \rangle = \frac{1}{Z_E} \cdot \frac{\rho_2^2 + 4Z_E^2}{1 + \sqrt{\rho_2^2 + Z_E^2} \sqrt{2\mu_A/Z_E}} \quad (11)$$

In this case, these two equations, Eqs. (10), (11), are independent of each other and include the unknowns of absorption coefficient $\mu_A$ and transport scattering coefficient $\mu_{TS}$. Accordingly, solving these Eqs. (10), (11) as simultaneous equations, the absorption coefficient $\mu_A$ and transport scattering coefficient $\mu_{TS}$ each can be calculated. The computation for solving these simultaneous equations can be executed at high speed utilizing a computer, and in addition, computation accuracy can be improved by performing measurement of mean optical pathlengths <L ($\rho$)> corresponding to many mutually different incidence-detection distances $\rho$.

The above description concerned the case where the scattering medium occupied the half space. In practice the size of the scattering medium is, however, finite. In this event, the boundary conditions for the photon diffusion equation represented by Eq. (4) are realized by placing a point light source of the first negative polarity to the surface and the outside of the scattering medium at the position ($\rho$=0, z=-z$_0$). A necessary condition for most light diffusively propagating in the scattering medium to satisfy the condition of light diffusion is to use a sufficiently large scattering medium.

Figure 5:
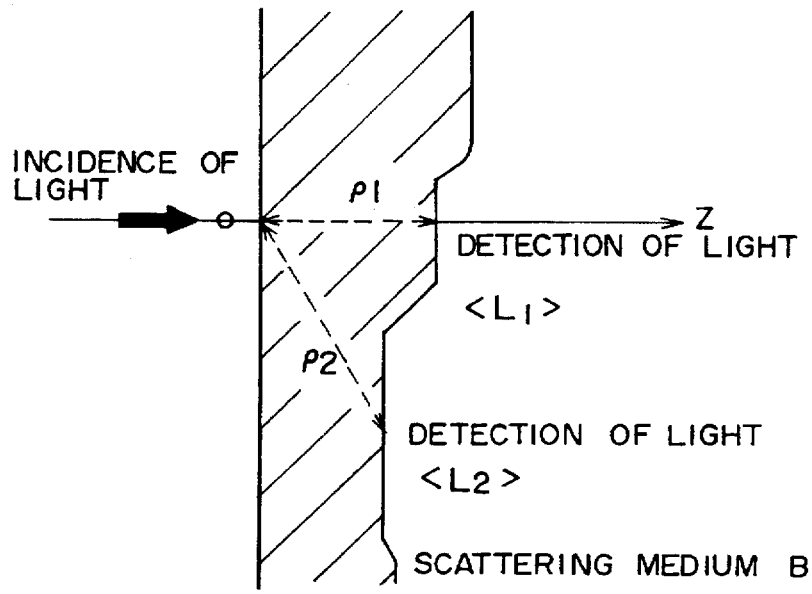
FIG. 5 is a sectional view to diagrammatically show a principle of measuring a mean optical pathlength in a slab scattering medium.

As shown in FIG. 5, if the thickness of the scattering medium B cannot be assumed as sufficiently larger than incidence-detection distances, that is, if the scattering medium B is of a slab shape, the boundary conditions for the photon diffusion equation represented by Eq. (4) may be realized by introducing point light sources of the second negative polarity and positive polarity on the back side opposed to the surface of the scattering medium B where the light source of the first negative polarity is set. In order to correct influence of the point light sources of the second negative polarity and positive polarity on the measuring light, an infinite number of point light sources need to be set theoretically. However, because the influence of these point light sources on the measuring light quickly decreases with an increase in the setting order, it can be approximated by setting a finite number of point light sources in practice.

Thus, a solution of the photon diffusion equation represented by Eq. (4) based on such boundary conditions is obtained as a light intensity I ($\rho$, 0, t) [number of photons·mm$^{-2}$·sec$^{-1}$] at an arbitrary position ($\rho$, 0) on the surface of the scattering medium and at time t, as indicated by Eq. (12).

$$I(\rho,0,t) = (4\pi Dc)^{-1/2} t^{-3/2} \exp(-\mu_A ct) \times \quad (12)$$

$$\left\{ (d - z_0)\exp\left[ -\frac{(d - z_0)^2}{4Dct} \right] - \right.$$

$$(d + z_0)\exp\left[ -\frac{(d + z_0)^2}{4Dct} \right] +$$

$$(3d - z_0)\exp\left[ -\frac{(3d - z_0)^2}{4Dct} \right] -$$

-continued $$(3d+z_0)\exp\left[-\frac{(3d+z_0)^2}{4Dct}\right]\Big\}$$

Here, substituting Eq. (12) into Eq. (8), we can derive an equation indicating the mean optical pathlength $<L(\rho)>$ of photons as to incidence of impulse light, that is, one corresponding to Eq. (9). The mean optical pathlength $<L(\rho)>$ represented by such an equation is expressed, similarly as in the aforementioned case, by one known that can be controlled or set, the incidence-detection distance $\rho$, and two unknowns to be measured, the absorption coefficient $\mu_A$ and transport scattering coefficient $\mu_{TS}$. Thus, if the incidence-detection distance $\rho$ is controlled or set to two or more different values and if two or more mean optical pathlengths $<L(\rho)>$ are calculated by Eq. (8) based on the time-resolved measurement of light intensity, the absorption coefficient $\mu_A$ and transport scattering coefficient $\mu_{TS}$ can be calculated based on the simultaneous relations consisting of two or more theoretical equations. The computation for solving such simultaneous equations can be executed at high speed utilizing a computer, similarly as in the aforementioned case, and in addition, the computation accuracy can be improved by performing measurement of mean optical pathlengths $<L(\rho)>$ corresponding to many mutually different incidence-detection distances $\rho$.

Further, a scattering coefficient and an absorption coefficient in the scattering medium are calculated as respective mean values along the optical path of light having diffusively propagated between the light incidence position and the light detection position. In some cases, three-dimensional distributions of these scattering and absorption coefficients are dispersed sufficiently rough as compared with the incidence-detection distances, the distances between plural light incidence positions, or the distances between plural light detection positions. If the measurement is done as scanning the surface of the scattering medium to change the light incidence position and light detection position, spatial distributions of scattering coefficient and absorption coefficient can be imaged, that is, simple imaging can be made therefor. If such measurement is carried out at different times, temporal changes of scattering coefficient and absorption coefficient can be monitored. Such imaging operation can be executed at high speed utilizing a computer having a memory, a display, etc.

(1.2) Principle for measuring concentration of absorptive constituent

Specific explanation is given as applying a living tissue as a scattering medium.

Figure 6:
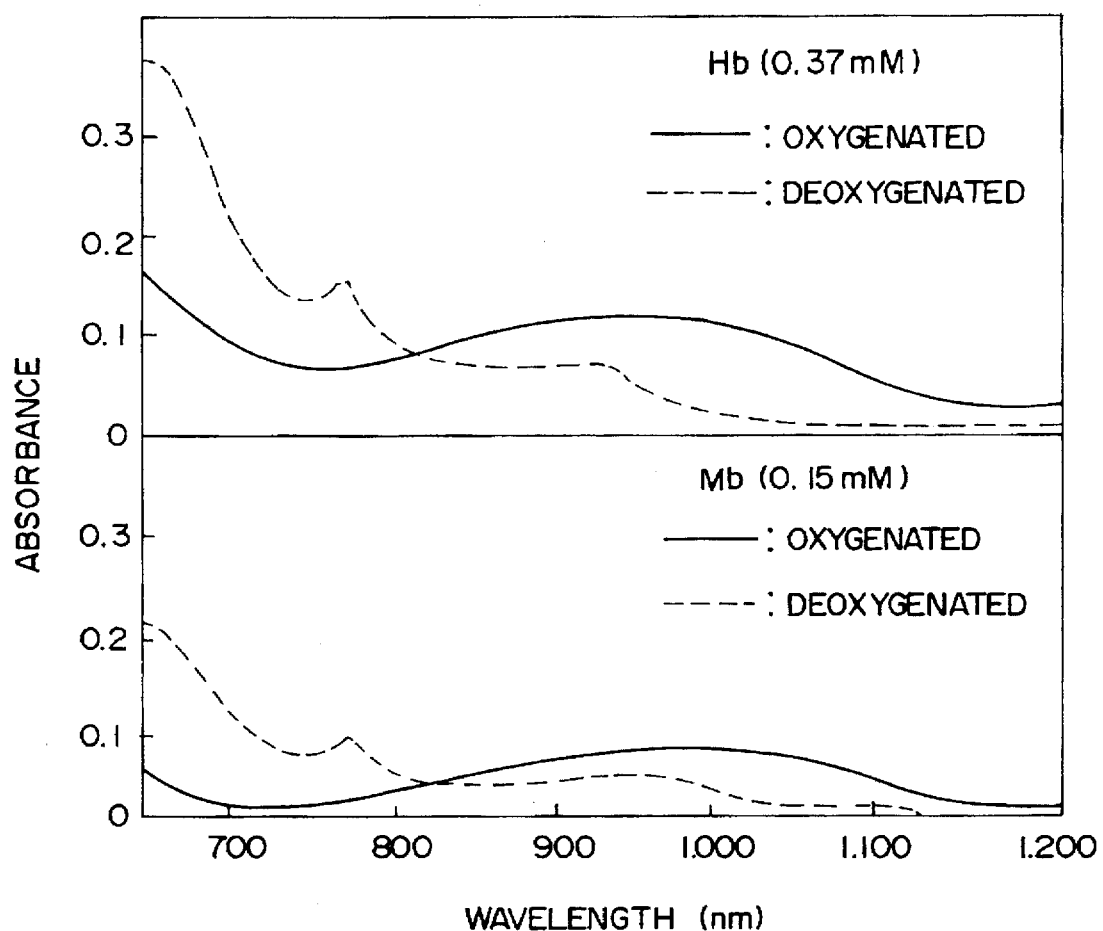
FIG. 6 is a graph to show near-infrared absorption spectra of hemoglobin and myoglobin.

As shown in FIG. 6, hemoglobin (Hb, $HbO_2$) and myoglobin (Mb, $MbO_2$), which are absorptive constituents in a living tissue, have characteristic absorption spectra depending upon the wavelength of light. Such absorption spectra change depending upon the type of absorptive constituent or a state of oxidation or reduction.

A mammal brain, which is a kind of living tissue, contains main absorptive constituents of water, cytochrome, deoxygenated hemoglobin Hb, and oxygenated hemoglobin $HbO_2$. Absorbances of water and cytochrome for near-infrared light are small enough to be ignored as compared with those of deoxygenated hemoglobin Hb and oxygenated hemoglobin $HbO_2$. Absorption spectra of deoxygenated hemoglobin Hb and oxygenated hemoglobin $HbO_2$ are different from each other, as described previously. Cranial bones can be considered as scattering media to near-infrared light.

Here, the absorption coefficient $\mu_A(\lambda)$ in a scattering medium to light having a wavelength $\lambda$ is expressed as shown in Eq. (13), based on the Beer-Lambert's law.

$$\mu_A(\lambda)=\epsilon_{Hb}(\lambda)[Hb]+\epsilon_{HbO2}(\lambda)[HbO_2] \qquad (13)$$

In the above equation, $\mu_A(\lambda)$: the absorption coefficient to the wavelength $\lambda$ [$mm^{-1}$], $\epsilon_{Hb}\ \lambda$: a molar absorption coefficient of deoxygenated hemoglobin Hb to the wavelength $\lambda$ [$mm^{-1}\cdot mM^{-1}$], $\epsilon_{HbO2}(\lambda)$: a molar absorption coefficient of oxygenated hemoglobin $HbO_2$ to the wavelength $\lambda$ [$mm^{-1}\cdot mM^{-1}$],

[Hb]: a molar concentration of deoxygenated hemoglobin Hb [mM],

[$HbO_2$]: a molar concentration of oxygenated hemoglobin $HbO_2$ [mM].

The absorption coefficient $\mu_A(\lambda)$ represented by Eq. (13) is expressed by two knowns that can be measured, the molar absorption coefficients $\epsilon_{Hb}(\lambda)$, $\epsilon_{HbO2}(\lambda)$ of deoxygenated hemoglobin Hb and oxygenated hemoglobin $HbO_2$, and two unknowns to be measured, the molar concentrations [Hb], [$HbO_2$] of deoxygenated hemoglobin Hb and oxygenated hemoglobin $HbO_2$. Thus, if the molar absorption coefficients $\epsilon_{Hb}(\lambda)$, $\epsilon_{HbO2}(\lambda)$ of deoxygenated hemoglobin Hb and oxygenated hemoglobin $HbO_2$ are measured for light having two or more different wavelengths $\lambda$ and if the absorption coefficients $\mu_A(\lambda)$ in the scattering medium are measured for the light having two or more different wavelengths $\lambda$, the molar concentrations [Hb], [$HbO_2$] of deoxygenated hemoglobin Hb and oxygenated hemoglobin $HbO_2$ can be calculated based on simultaneous relations consisting of two or more Equations (13).

More specifically, the above-discussed time-resolved measurement of measuring light is carried out for light having two different wavelengths $\lambda_1$, $\lambda_2$ in a scattering medium, and absorption coefficients $\mu_A(\lambda_1)$, $\mu_A(\lambda_2)$ in the scattering medium are measured. Subsequently, substituting a combination of absorption coefficient $\mu_A(\lambda_1)$ and already known molar absorption coefficients $\epsilon_{Hb}(\lambda_1)$, $\epsilon_{HbO2}(\lambda_1)$ and a combination of absorption coefficient $\mu_A(\lambda_2)$ and already known molar absorption coefficients $\epsilon_{Hb}(\lambda_2)$, $\epsilon_{HbO2}(\lambda_2)$ each into Eq. (13), the following simultaneous relations as indicated by Eqs. (14), (15) can be obtained.

$$\mu_A(\lambda_1)=\epsilon_{Hb}(\lambda_1)[Hb]+\epsilon_{HbO2}(\lambda_1)[HbO_2] \qquad (14)$$

$$\mu_A(\lambda_2)=\epsilon_{Hb}(\lambda_2)[Hb]+\epsilon_{HbO2}(\lambda_2)[HbO_2] \qquad (15)$$

In this case, these two equations, Eqs. (14), (15), are independent of each other and include unknowns of the molar concentrations [Hb], [$HbO_2$]. Therefore, by solving these Equations (14), (15) as simultaneous equations, the molar concentrations [Hb], [$HbO_2$] of deoxygenated hemoglobin Hb and oxygenated hemoglobin $HbO_2$, and a total molar concentration of hemoglobin ([Hb]+[$HbO_2$]) can be calculated. Computation for solving such simultaneous equations can be executed at high speed utilizing a computer, and in addition, the computation accuracy can be improved by measuring the absorption coefficients $\mu_A(\lambda)$ for light having many mutually different wavelengths $\lambda$.

A hemoglobin oxygen saturation Y (%) for such deoxygenated hemoglobin Hb and oxygenated hemoglobin $HbO_2$ is defined as indicated by Eq. (16).

$$Y=\{[HbO_2]/([Hb]+[HbO_2])\}\times 100 \qquad (16)$$

Thus, a ratio of absorption coefficients $\mu_A(\lambda_1)$, $\mu_A(\lambda_2)$ is given by Eq. (17) from Eqs. (14) to (16).

$$\frac{\mu_A(\lambda_1)}{\mu_A(\lambda_2)} = \frac{\epsilon_{Hb}(\lambda_1) + Y[\epsilon_{HbO2}(\lambda_1) - \epsilon_{Hb}(\lambda_1)]/100}{\epsilon_{Hb}(\lambda_2) + Y[\epsilon_{HbO2}(\lambda_2) - \epsilon_{Hb}(\lambda_2)]/100} \quad (17)$$

Accordingly, modifying (17), the hemoglobin oxygen saturation Y (%) for deoxygenated hemoglobin Hb and oxygenated hemoglobin HbO$_2$ is given as indicated by Eq. (18).

$$Y = \frac{\mu_A(\lambda_2)\epsilon_{Hb}(\lambda_1) - \mu_A(\lambda_1)\epsilon_{Hb}(\lambda_2)}{\mu_A(\lambda_1)E_{11} + \mu_A(\lambda_2)E_{22}} \times 100 \quad (18)$$

In the above equation, $E_{11} = \epsilon_{HbO2}(\lambda_1) - \epsilon_{Hb}(\lambda_1)$, $E_{22} = \epsilon_{HbO2}(\lambda_2) - \epsilon_{Hb}(\lambda_2)$.

The hemoglobin oxygen saturation Y represented by Eq. (18) is expressed by measurable knowns including four molar absorption coefficients $\epsilon_{Hb}(\lambda_1)$, $\epsilon_{HbO2}(\lambda_1)$, $\epsilon_{Hb}(\lambda_2)$, $\epsilon_{HbO2}(\lambda_2)$ of deoxygenated hemoglobin Hb and oxygenated hemoglobin HbO$_2$ and two absorption coefficients $\mu_A(\lambda_1)$, $\mu_A(\lambda_2)$ in the scattering medium for the two different wavelengths $\lambda_1$, $\lambda_2$ of light, and thus, can be calculated easily.

Now, there are some living tissues which include unignorable influence of an absorptive constituent other than hemoglobin. Adding a term of background absorption, $\alpha(\lambda)$, to the light having the wavelength $\lambda$ to the right side of Eq. (13), the absorption coefficient $\mu_A(\lambda)$ in the scattering medium to the light having the wavelength $\lambda$ is expressed as indicated by the following Equation (19).

$$\mu_A(\lambda) = \epsilon_{Hb}(\lambda)[Hb] + \epsilon_{HbO2}(\lambda)[HbO_2] + \alpha(\lambda) \quad (19)$$

The absorption coefficient $\mu_A(\lambda)$ represented by Eq. (19) is expressed by two knowns that can be measured, the molar absorption coefficients $\epsilon_{Hb}(\lambda)$, $\epsilon_{HbO2}(\lambda)$ of deoxygenated hemoglobin Hb and oxygenated hemoglobin HbO$_2$, two unknowns to be measured, the molar concentrations [Hb], [HbO$_2$] of deoxygenated hemoglobin Hb and oxygenated hemoglobin HbO$_2$, and one background absorption term $\alpha(\lambda)$. Thus, if the molar absorption coefficients $\epsilon_{Hb}(\lambda)$, $\epsilon_{HbO2}(\lambda)$ of deoxygenated hemoglobin Hb and oxygenated hemoglobin HbO$_2$ are measured for light having three or more different wavelengths $\lambda$ and if the absorption coefficients $\mu_A(\lambda)$ in the scattering medium are measured for the light having the three or more different wavelengths $\lambda$, the molar concentrations [Hb], [HbO$_2$] of deoxygenated hemoglobin Hb and oxygenated hemoglobin HbO$_2$ can be calculated based on simultaneous relations consisting of three or more Equations (19).

More specifically, the previously discussed time-resolved measurement of measuring light is carried out for light having three different wavelengths $\lambda_1$, $\lambda_2$, $\lambda_3$ in the scattering medium, thereby measuring absorption coefficients $\mu_A(\lambda_1)$, $\mu_A(\lambda_2)$, $\mu_A(\lambda_3)$ in the scattering medium. Subsequently, substituting a combination of the absorption coefficient $\mu_A(\lambda_1)$ and already known molar absorption coefficients $\epsilon_{Hb}(\lambda_1)$, $\epsilon_{HbO2}(\lambda_1)$, a combination of the absorption coefficient $\mu_A(\lambda_2)$ and molar absorption coefficients $\epsilon_{Hb}(\lambda_2)$, $\epsilon_{HbO2}(\lambda_2)$, and a combination of the absorption coefficient $\mu_A(\lambda_3)$ and molar absorption coefficients $\epsilon_{Hb}(\lambda_3)$, $\epsilon_{HbO2}(\lambda_3)$ each into Eq. (19), simultaneous relations represented by Eqs. (20) to (22) can be obtained.

$$\mu_A(\lambda_1) = \epsilon_{Hb}(\lambda_1)[Hb] + \epsilon_{HbO2}(\lambda_1)[HbO_2] + \alpha(\lambda_1) \quad (20)$$

$$\mu_A(\lambda_2) = \epsilon_{Hb}(\lambda_2)[Hb] + \epsilon_{HbO2}(\lambda_2)[HbO_2] + \alpha(\lambda_2) \quad (21)$$

$$\mu_A(\lambda_3) = \epsilon_{Hb}(\lambda_3)[Hb] + \epsilon_{HbO2}(\lambda_3)[HbO_2] + \alpha(\lambda_3) \quad (22)$$

On this occasion, these three Equations (20) to (22) are independent of each other and in addition, they include the unknowns of molar concentrations [Hb], [HbO$_2$] and background absorption terms $\alpha(\lambda_1)$, $\alpha(\lambda_2)$, $\alpha(\lambda_3)$. Here, the three different wavelengths $\lambda_1$, $\lambda_2$, $\lambda_3$ can be preliminarily set so that the background absorption terms $\alpha(\lambda_1)$, $\alpha(\lambda_2)$, $\alpha(\lambda_3)$ become coincident with each other. Accordingly, solving these Equations (20) to (22) as simultaneous equations, we can calculate the molar concentrations [Hb], [HbO$_2$] of deoxygenated hemoglobin Hb and oxygenated hemoglobin HbO$_2$ and the total molar concentration of hemoglobin ([Hb]+[HbO$_2$]). The computation to solve these simultaneous equations can be executed at high speed utilizing a computer.

A ratio of differences of the absorption coefficients $\mu_A(\lambda_1)$, $\mu_A(\lambda_3)$ from the absorption coefficient $\mu_A(\lambda_2)$ are given by Eq. (23) from Eqs. (20) to (22).

$$\frac{\mu_A(\lambda_1) - \mu_A(\lambda_2)}{\mu_A(\lambda_3) - \mu_A(\lambda_2)} = \frac{E_{12} + Y(E_{11} + E_{22})/100 + [\alpha(\lambda_1) - \alpha(\lambda_2)]}{E_{32} + Y(E_{33} + E_{22})/100 + [\alpha(\lambda_3) - \alpha(\lambda_2)]} \quad (23)$$

In the above equation, $E_{33} = \epsilon_{HbO2}(\lambda_3) - \epsilon_{Hb}(\lambda_3)$, $E_{12} = \epsilon_{Hb}(\lambda_1) - \epsilon_{Hb}(\lambda_2)$, $E_{22} = \epsilon_{Hb}(\lambda_3) - \epsilon_{Hb}(\lambda_2)$, If the three different wavelengths $\lambda_1$, $\lambda_2$, $\lambda_3$ are preliminarily set so that the background absorption terms $\alpha(\lambda_1)$, $\alpha(\lambda_2)$, $\alpha(\lambda_3)$ become coincident with each other, Eq. (23) is modified as shown in Eq. (24).

$$\frac{\mu_A(\lambda_1) - \mu_A(\lambda_2)}{\mu_A(\lambda_3) - \mu_A(\lambda_2)} = \frac{E_{12} + Y(E_{11} - E_{22})/100}{E_{32} + Y(E_{33} - E_{22})/100} \quad (24)$$

Accordingly, the hemoglobin oxygen saturation Y (%) for deoxygenated hemoglobin Hb and oxygenated hemoglobin HbO$_2$ is given by Eq. (25), modifying Eq. (24).

In the above equation, $$Y = \left\{ \frac{\mu_A(\lambda_1) - \mu_A(\lambda_2)}{\mu_A(\lambda_3) - \mu_A(\lambda_2)} (E_{32} - E_{12}) \right\} / \quad (25)$$

$$\left\{ \frac{\mu_A(\lambda_1) - \mu_A(\lambda_2)}{\mu_A(\lambda_3) - \mu_A(\lambda_2)} (E_{33} - E_{22}) - (E_{11} - E_{22}) \right\} \times 100$$

$E_{32} = \epsilon_{Hb}(\lambda_3) - \epsilon_{Hb}(\lambda_2)$.

The hemoglobin oxygen saturation Y represented by this Eq. (25) is expressed by knowns that can be measured, the six molar absorption coefficients $\epsilon_{Hb}(\lambda_1)$, $\epsilon_{HbO2}(\lambda_1)$, $\epsilon_{Hb}(\lambda_2)$, $\epsilon_{HbO2}(\lambda_2)$, $\epsilon_{Hb}(\lambda_3)$, $\epsilon_{HbO2}(\lambda_3)$ of deoxygenated hemoglobin Hb and oxygenated hemoglobin HbO$_2$ for the three different wavelengths $\lambda_1$, $\lambda_2$, $\lambda_3$ of light and the three absorption coefficients $\mu_A(\lambda_1)$, $\mu_A(\lambda_2)$, $\mu_A(\lambda_3)$ in the scattering medium, and thus, it can be calculated easily.

(2) Apparatus for measuring scattering property and absorption property in scattering medium (2.1) First embodiment The present embodiment is a measuring apparatus for measuring the scattering property and absorption property in the interior of a scattering medium which is sufficiently larger than incidence-detection distances.

Figure 7:
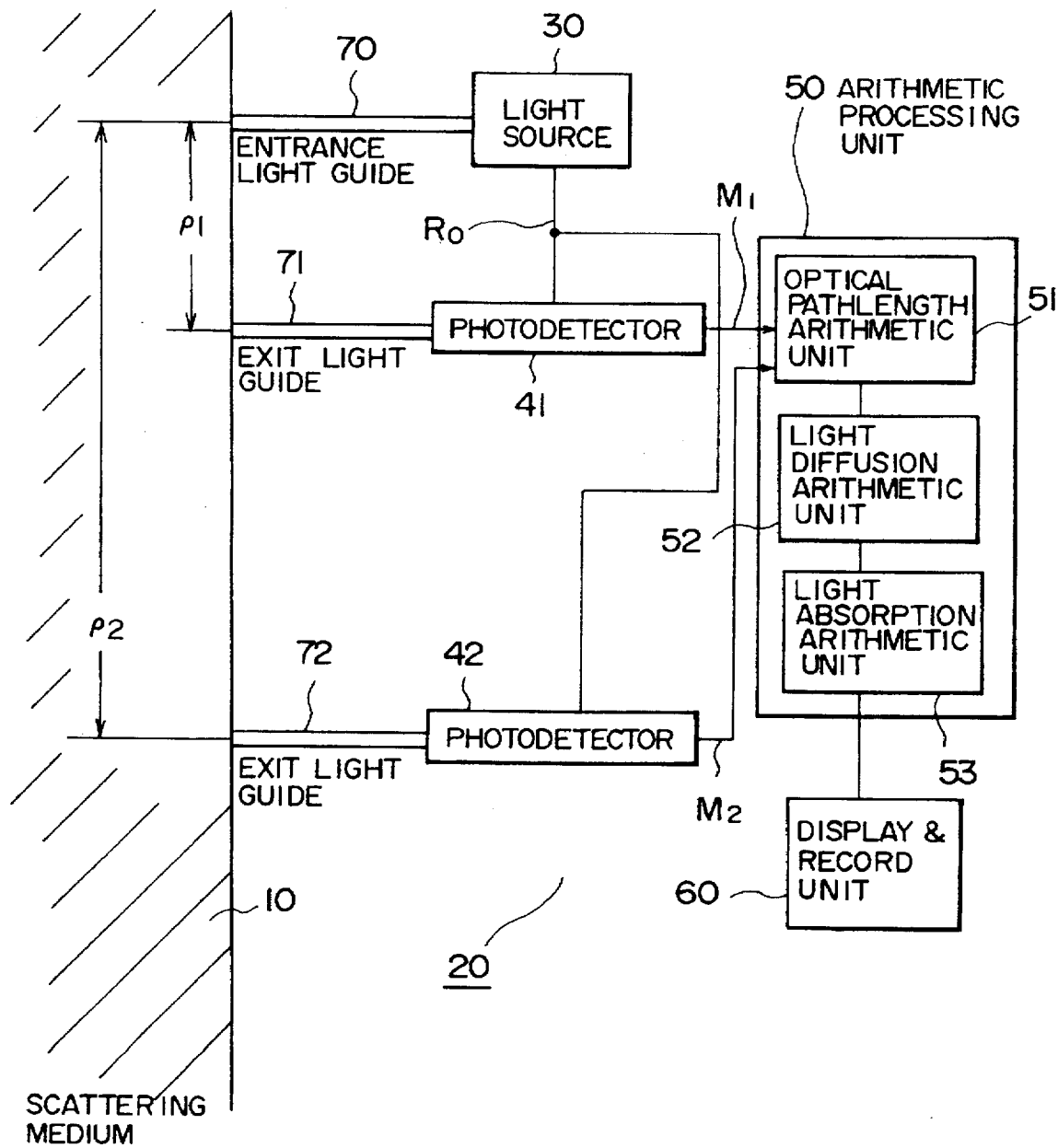
FIG. 7 is a sectional view to diagrammatically show an apparatus for measuring the scattering property and absorption property in the scattering medium.
Figure 8A:
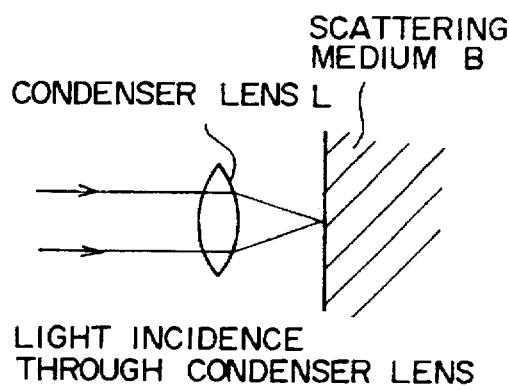
FIG. 8A to FIG. 8D are sectional views to diagrammatically show various means used as a method for guiding light into the scattering medium in the measuring apparatus of FIG. 7.
Figure 8B:
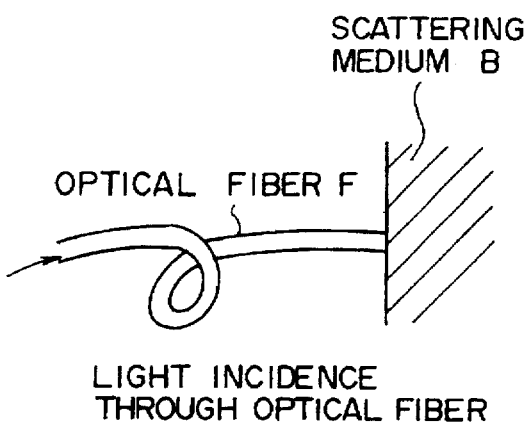
Figure 8C:
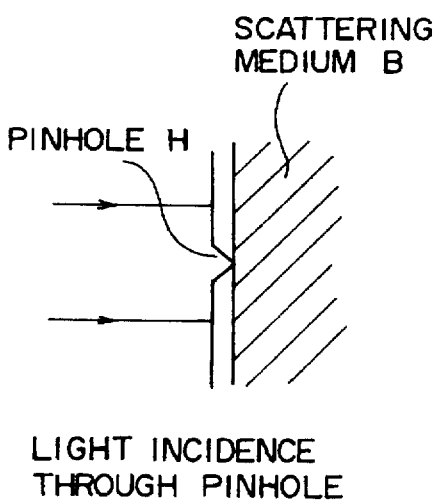
Figure 8D:
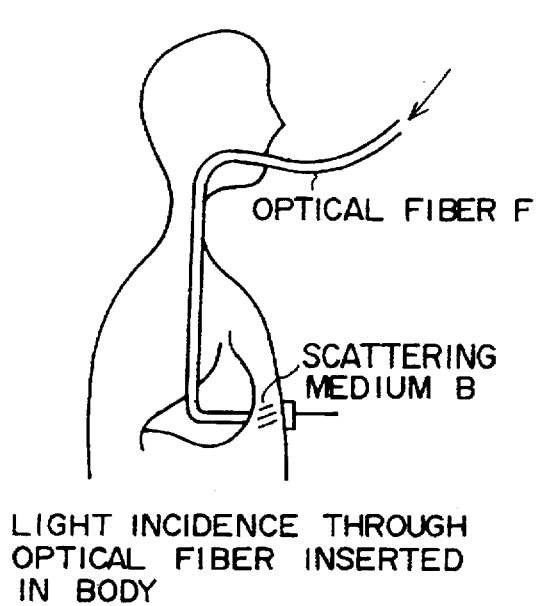

As shown in FIG. 7, the measuring apparatus 20 is composed of a light source 30 for emitting measuring light $P_0$, an entrance light guide 70 for guiding the measuring light $P_0$ into the scattering medium 10, two exit light guides 71, 72 for guiding the measuring light $P_0$ having diffusively propagated inside the scattering medium 10 out thereof, two photodetectors 41, 42 for detecting the measuring light $P_0$ through photoelectric conversion, and a signal processing system for processing electric signals output from these photodetectors 41, 42. This signal processing system includes an arithmetic processing unit 50 for executing various arithmetic processes concerning the scattering property and absorption property in the interior of the scattering medium 10, and a display record unit 60 for displaying or recording various data calculated by the arithmetic processes.

The light source 30 has a wavelength controlling means for generating the measuring light $P_0$ of pulsed light of (N+1) different wavelengths $\lambda_1, \lambda_2, \ldots, \lambda_{N+1}$ at frequency f for a number N of types of absorptive constituents contained in the scattering medium 10, and is a laser diode for outputting a reference signal $R_0$ synchronized with pulse oscillation of the measuring light $P_0$ to the photodetectors 41, 42. The wavelengths $\lambda_1, \ldots, \lambda_{N+1}$ of the measuring light $P_0$ need to be properly selected in accordance with the composition of the scattering medium 10.

For example, let us consider a case where the scattering medium 10 is a living tissue. Since hemoglobin and myoglobin have large absorbances to the light of wavelengths of about 700 nm to about 1000 nm, it is preferable that the wavelengths $\lambda_1, \ldots, \lambda_{N+1}$ of the measuring light $P_0$ be set in the near-infrared region, from the viewpoint of improving the measurement accuracy. Further, because these hemoglobin and myoglobin show different light absorption spectra depending upon oxidized or reduced states thereof, it is preferable that the wavelengths $\lambda_1, \ldots, \lambda_{N+1}$ of the measuring light $P_0$ be set apart from each other, from the viewpoint of discriminating measuring objects from each other.

As long as such control is possible for the wavelengths $\lambda_1, \ldots, \lambda_{N+1}$ of the measuring light $P_0$, the light source 30 can be selected from a variety of light sources including light-emitting diodes.

The entrance light guide 70 converges the measuring light $P_0$ incident from the light source 30 into a spot and then outputs it into the scattering medium 10. As shown in FIG. 8A to FIG. 8D, a specific light guiding means into the scattering medium B, which can replace the entrance light guide 70, is one selected from arrangements in which a condenser lens L (see FIG. 8A), an optical fiber F (see FIG. 8B), or a pinhole H (see FIG. 8C) is set near or on the surface of the scattering medium B and an arrangement in which an optical fiber F is inserted into the scattering medium such as a human body, like a gastrocamera (see FIG. 8D).

For example, if the scattering medium 10 is a living tissue, the measuring light $P_0$ is scattered before it travels straight by the mean diffusion length of about 2 mm inside the scattering medium 10. Therefore, if the size of the scattering medium 10 is sufficiently larger than the mean diffusion length, influence of the mean diffusion length on the directivity of the measuring light $P_0$ can be ignored when the spot measuring light $P_0$ is emitted into the scattering medium 10. If relatively thick beam light can be regarded as a plurality of spot light beams juxtaposed, the measuring light $P_0$ can be suitably emitted in a beam shape into the scattering medium 10.

Figure 9A:
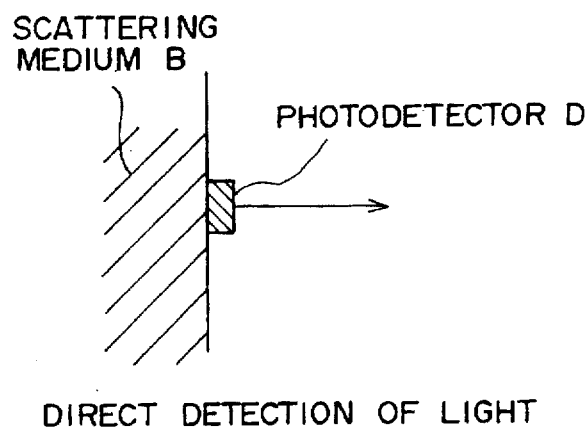
FIG. 9A to FIG. 9C are sectional views to diagrammatically show various means used as a method for guiding light from the scattering medium in the measuring apparatus of FIG. 7.
Figure 9B:
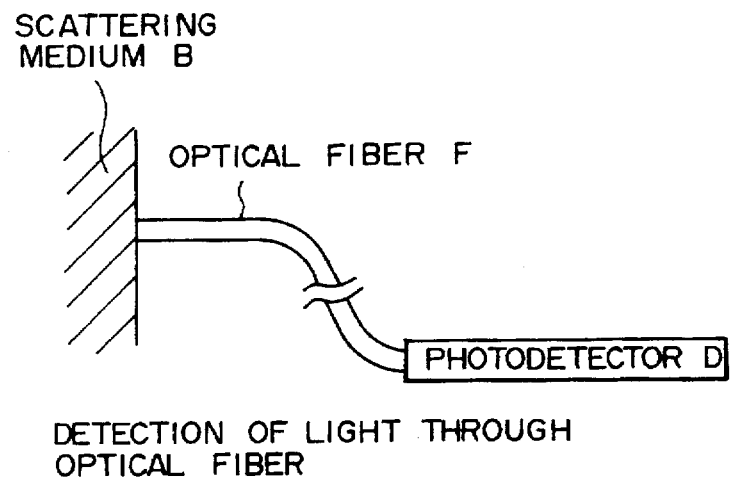
Figure 9C:
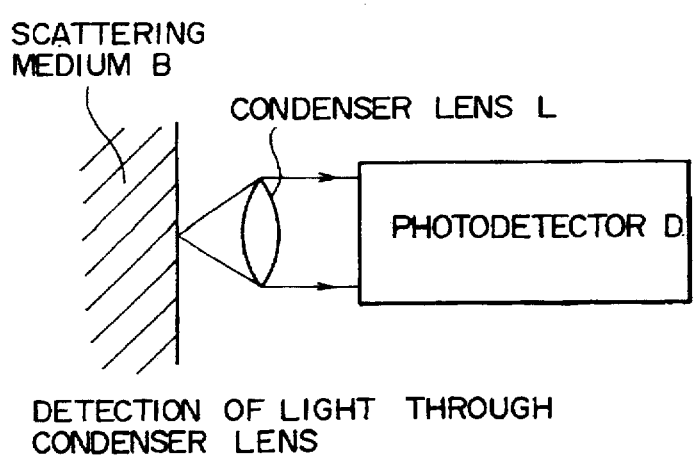

The two exit light guides 71, 72 take the measuring light $P_0$ having diffusively propagated in the interior of the scattering medium 10 out thereof and guide it to the two photodetectors 41, 42, respectively. As shown in FIG. 9A to FIG. 9C, a specific light guiding means from the scattering medium, that can replace the two exit light guide 71, 72, is one selected from an arrangement in which a photodetector D is directly set on the surface of the scattering medium B (see FIG. 9A) and arrangements in which an optical fiber F (see FIG. 9B) or a condenser lens L (see FIG. 9C) is set on or near the surface of the scattering medium B.

Here, the physical distance between the light incidence position, where the entrance light guide 70 is set on the surface of the scattering medium 10, and the light detection positions, where the two exit light guide 71, 72 are set on the surface of the scattering medium 10, should be set to different incidence-detection distances $\rho_1, \rho_2$. It is also preferable that a liquid body or a jelly body, which has a refractive index and a scattering coefficient substantially coincident with or close to those of the scattering medium 10, be interposed as an interface member between the scattering medium 10 and the entrance light guide 70 or the two exit light guides 71, 72. In this case, by properly selecting the interface member, influence due to surface reflection on the scattering medium 10 can be reduced for the measuring light $P_0$ having diffusively propagated inside the interface member.

The two photodetectors 41, 42 are those for sampling the measuring light $P_0$ guided thereto through the two exit light guides 71, 72, based on the reference signal $R_0$ coming from the light source 30, photoelectrically converting it into electric signals, and then outputting detection signals $M_1$, $M_2$ of the time-resolved measurement to the arithmetic processing unit 50. It is necessary to set relatively large spectral sensitivity characteristics and gains of the two photodetectors 40, 41 in order to well detect the wavelengths $\lambda_1, \ldots, \lambda_{N+1}$ of the measuring light $P_0$. It is also necessary that response frequencies of the two photodetectors 40, 41 be set as high as possible in order to well perform the time-resolved measurement of the measuring light $P_0$. Further, if the measuring light $P_0$ having diffusively propagated inside the scattering medium 10 has plural different wavelengths because of generation of fluorescence, it becomes necessary to set a wavelength selection filter between the each two photodetector 40, 41 and the scattering medium 10.

As long as detection is possible for the wavelengths $\lambda_1, \ldots, \lambda_{N+1}$ of the measuring light $P_0$, the two photodetectors 40, 41 can be selected from various detectors including avalanche photodiodes, PIN photodiodes, streak cameras, phototubes, multiplier phototubes, etc.

The arithmetic processing unit 50 is one for performing various arithmetic processes based on the detection signals $M_1, M_2$ from the two photodetectors 40, 41 and outputs results as data signals $D_0$ to the display record unit 60. The arithmetic processing unit 50 includes an optical pathlength arithmetic unit 51 for calculating mean optical pathlengths $<L(\rho_1)>$, $<L(\rho_2)>$ of the measuring light $P_0$ corresponding to the wavelengths $\lambda_1, \ldots, \lambda_{N+1}$ of the measuring light $P_0$ and the incidence-detection distances $\rho_1, \rho_2$, a light diffusion arithmetic unit 52 for calculating transport scattering coefficients $\mu_{TS}(\lambda_1), \mu_{TS}(\lambda_2), \ldots, \mu_{TS}(\lambda_{N+1})$ and absorption coefficients $\mu_A(\lambda_1), \mu_A(\lambda_2), \ldots, \mu_A(\lambda_{N+1})$ inside the scattering medium 10 based on a plurality of simultaneous relations consisting of theoretical equations of these mean optical pathlengths $<L(\rho_1)>$, $<L(\rho_2)>$, and a light absorption arithmetic unit 53 for calculating concentrations [AC (1)], [AC (2)], ..., [AC (N)] of N absorptive constituents AC (1), AC (2), ..., AC (N) contained in the scattering medium 10, based on plural simultaneous relations consisting of theoretical equations of these absorption coefficients $\mu_A(\lambda_1), \ldots, \mu_A(\lambda_{N+1})$.

The display record unit 60 includes a console monitor, a printer, and a memory for displaying or recording the transport scattering coefficients $\mu_{TS}(\lambda_1), \ldots, \mu_{TS}(\lambda_{N+1})$ and absorption coefficients $\mu_A(\lambda_1), \ldots, \mu_A(\lambda_{N+1})$ or the concentrations [AC (1)], ..., [AC (N)] of absorptive constituents, based on the data signals $D_0$ sent from the arithmetic processing unit 50.

If the wavelengths of the measuring light $P_0$ are set in time division as sequentially selecting $\lambda_1, \ldots, \lambda_{N+1}$, a wavelength selector set for the light source 30 may be a light beam switching unit using a mirror or a light switching unit using an optical switch. In contrast, if the measuring light $P_0$ simultaneously includes the all wavelengths of $\lambda_1, \ldots, \lambda_{N+1}$, the wavelength selector set for the light source 30 or the two photodetectors 40, 41 may be a wavelength switching unit using a filter. In this case, if there are a multiplicity of combinations of wavelength selectors and photodetectors employed, the time-resolved measurement can be carried out in parallel for the wavelengths $\lambda_1, \ldots, \lambda_{N+1}$ of the measuring light $P_0$.

In order to amplify the detection signals $M_1, M_2$ with low noise, an amplifier may be provided for the two photodetector 40, 41, which may be a narrow band amplifier or a lock-in amplifier. Particularly, with the lock-in amplifier, measurement can be done in a high dynamic range for the pulsed measuring light $P_0$.

The operation of the present embodiment is next explained.

In the measuring apparatus 20 as constructed in the above structure, the light source 30 emits the pulsed measuring light $P_0$ having the (N+1) different wavelengths $\lambda_1, \ldots, \lambda_{N+1}$ at frequency f, and the measuring light is guided through the entrance light guide 70 into the scattering medium 10. This light source 30 outputs the reference signal $R_0$ synchronized with the pulse oscillation of the measuring light $P_0$ to the arithmetic processing unit 50. Thus, the measuring light $P_0$ diffusively propagates inside the scattering medium 10 as expanding the pulse time width, and is taken out by the two exit light guides 71, 72 at light detection positions two different physical distances $\rho_1, \rho_2$ apart from the light incidence position.

Here, the two photodetectors 41, 42 set a reference time $t_0$ as an oscillation timing of the measuring light $P_0$, based on the reference signal $R_0$ coming from the light source 30, and also set a measuring time $t_M = t_0 + \Delta t$ as a sampling timing of the measuring light $P_0$. These two photodetectors 41, 42 photoelectrically convert the measuring light $P_0$ received through the two exit light guides 71, 72 from the scattering medium 10, at the measuring time $t_M$, amplify respective detection signals $M_1, M_2$ having levels proportional to light intensities of the measuring light $P_0$, and output the thus amplified signals to the arithmetic processing unit 50. Subsequently, the two photodetectors 40, 41 perform sequential samplings while setting reference times $t_B = t_0 + (M-1)/f$ and measuring times $t_M = t_0 + (M-1)/f + M \cdot \Delta t$, thus performing the time-resolved measurement of the measuring light $P_0$ as continuous operation. Here, $M = 1, 2, 3, \ldots$.

In the case where the two photodetectors 41, 42 performs measurement of light intensity, each level of detection signal $M_1, M_2$ is proportional to a light intensity of the measuring light $P_0$ at each measurement time $t_M$. Further, if the two photodetectors 41, 42 performs measurement of number of photons, each level of detection signal $M_1, M_2$ is proportional to a number of photons of the measuring light $P_0$ at each measurement time $t_M$.

The optical pathlength arithmetic unit 51 disposed in the arithmetic processing unit 50 calculates the mean optical pathlengths $<L (\rho_1)>, <L (\rho_2)>$ corresponding to the wavelengths $\lambda_1, \ldots, \lambda_{N+1}$ of the measuring light $P_0$ and the incidence-detection distances $\rho_1, \rho_2$, using Eq. (26) or Eq. (27) as being a simplified form of Eq. (8), based on the detection signals $M_1, M_2$ input thereinto at each sampling timing from the two photodetectors 41, 42, and outputs them to the light diffusion arithmetic unit 52.

$$\langle L \rangle = \frac{c \sum_M I(\rho, t_M) T_M}{\sum_M I(\rho, t_M)} \quad (26)$$

In the above equations, $T_M$: a time difference $M \cdot \Delta t$ between each reference $$\langle L \rangle = \frac{c \sum_M n(\rho, t_M) T_M}{\sum_M n(\rho, t_M)} \quad (27)$$

time $t_B$ and each measuring time $t_M$, $I (\rho, t_M)$: a light intensity of the measuring light $P_0$, $n (\rho, t_M)$: a number of photons of the measuring light $P_0$.

The light diffusion arithmetic unit 52 sequentially substitutes the calculation values of mean optical pathlengths $<L (\rho_1)>, <L (\rho_2)>$, calculated by the optical pathlength arithmetic unit 51, into Eq. (9), solves Eqs. (10), (11) as simultaneous equations to calculate the absorption coefficients $\mu_a (\lambda_1), \ldots, \mu_A (\lambda_{N+1})$ and transport scattering coefficients $\mu_{TS} (\lambda_1), \ldots, \mu_{TS} (\lambda_{N+1})$, and then outputs them to the light absorption arithmetic unit 53.

The light absorption arithmetic unit 53 sequentially substitutes the calculation values of the absorption coefficients $\mu_A (\lambda_1), \ldots, \mu_A (\lambda_{N+1})$ and transport scattering coefficients $\mu_{TS} (\lambda_1), \ldots, \mu_{TS} (\lambda_{N+1})$, calculated by the light diffusion arithmetic unit 52, into Eq. (28) as being an extended form of Eq. (13).

In the above equation, $\epsilon_{AC} (N) (\lambda)$: molar absorption coefficients of $$\mu_A(\lambda) = \epsilon_{AC(1)}(\lambda)[AC(1)] + \epsilon_{AC(2)}(\lambda)[AC(2)] + \ldots + \epsilon_{AC(N)}(\lambda)[AC(N)] \quad (28)$$

absorptive constituents AC (N) for the wavelength $\lambda$ [mm$^{-1} \cdot$M$^{-1}$],

[AC (N)]: molar concentrations of the absorptive constituents AC (N) [M].

The light absorption arithmetic unit 53 solves Eqs. (29) to (30) as simultaneous equations as being extended forms of Eqs. (14), (15) to calculate the concentrations [AC (1)], ..., [AC (N)] of N types of different absorptive constituents, and outputs them as data signals $D_0$ to the display record unit 60.

$$\mu_A(\lambda_1) = \epsilon_{AC(1)}(\lambda_1)[AC(1)] + \epsilon_{AC(2)}(\lambda_1)[AC(2)] + \ldots + \epsilon_{AC(N)}(\lambda_1)[AC(N)] \quad (29)$$

$$\mu_A(\lambda_N) = \epsilon_{AC(1)}(\lambda_N)[AC(1)] + \epsilon_{AC(2)}(\lambda_N)[AC(2)] + \ldots + \epsilon_{AC(N)}(\lambda_N)[AC(N)] \quad (30)$$

The display record unit 60 performs display or record concerning the calculation values of the absorption coefficients $\mu_A (\lambda_1), \ldots, \mu_A (\lambda_{N+1})$ and transport scattering coefficients $\mu_{TS} (\lambda_1), \ldots, \mu_{TS} (\lambda_{N+1})$ and the calculation values of the concentrations [AC (1)], ..., [AC (N)] of the N types of different absorptive constituents, coming from the light absorption arithmetic unit 53.

(2.2) Second embodiment

The present embodiment is a measuring apparatus for monitoring the concentration and oxygen saturation of hemoglobin as applying a human head as the scattering medium and an absorptive constituent of hemoglobin in the brain as a measuring object.

As shown in FIG. 10, the measuring apparatus 21 is unitarily fixed by a band type light guide holder 80 mounted around a scattering medium 10 of a human head. The light guide holder 80 is arranged to cover the periphery of the scattering medium 10 like a headband by adjusting the holder length according to the peripheral length of the scattering medium 10 by two holder length adjusters 81, 82. An inner space 83 formed inside the light guide holder 80 includes the light source 30, two photodetectors 41, 42, entrance light guide 70, and two exit light guides 71, 72 arranged in the same structure as in the above first embodiment. Disposed on the peripheral portion of the light guide holder 80 is a connector 90 for outputting the detection signals $M_1$, $M_2$ coming from the two photodetectors 41, 42 to the signal processing system (not shown). This signal processing system is composed of the arithmetic processing unit 50 and display record unit 60 arranged in the same manner as in the above first embodiment.

The scattering medium 10 is the brain of a man, which contains deoxygenated hemoglobin Hb and oxygenated hemoglobin $HbO_2$ as absorptive constituents. The light source 30 emits pulsed light having three different wavelengths $\lambda_1$, $\lambda_2$, $\lambda_3$ as measuring light $P_0$ to the two types of absorptive constituents in the scattering medium 10. The wavelengths $\lambda_1$–$\lambda_3$ of the measuring light $P_0$ need to be set so that they show different absorbances of deoxygenated hemoglobin Hb and oxygenated hemoglobin $HbO_2$ and so that the background absorption terms as described previously as influence due to absorptive constituents other than the two types of absorptive constituents are nearly equal to each other.

The operation of the present embodiment is next explained.

In the measuring apparatus 21 as constructed in the above structure, the light source 30 emits the pulsed measuring light $P_0$ having the three different wavelengths $\lambda_1$, $\lambda_2$, $\lambda_3$ at frequency f, and the measuring light is guided through the entrance light guide 70 into the scattering medium 10. This light source 30 outputs the reference signal $R_0$ synchronized with the pulse oscillation of the measuring light $P_0$ to the arithmetic processing unit 50. Thus, the measuring light $P_0$ diffusively propagates inside the scattering medium 10 as expanding the pulse time width, and is taken out by the two exit light guides 71, 72 at light detection positions two different physical distances $\rho_1$, $\rho_2$ apart from the light incidence position.

Here, the two photodetectors 41, 42 set the reference time $t_B=t_0$ as an oscillation timing of the measuring light $P_0$, based on the reference signal $R_0$ coming from the light source 30, and also set a measuring time $t_M=t_0+\Delta t$ as a sampling timing of the measuring light $P_0$. These two photodetectors 41, 42 photoelectrically convert the measuring light $P_0$ received through the two exit light guides 71, 72 from the scattering medium 10, at the measuring time $t_M$, amplify respective detection signals $M_1$, $M_2$ having levels proportional to light intensities of the measuring light $P_0$, and output the thus amplified signals to the arithmetic processing unit 50 trough the connector 90. Subsequently, the two photodetectors 40, 41 perform sequential samplings while setting reference times $t_B=t_0+(M-1)/f$ and measuring times $t_M=t_0+(M-1)/f+M\cdot\Delta t$, thus performing the time-resolved measurement of the measuring light $P_0$ as continuous operation. Here, M=1, 2, 3, . . . .

In the case where the two photodetector 41, 42 perform measurement of light intensity, each level of detection signal $M_1$, $M_2$ is proportional to a light intensity of the measuring light $P_0$ at each measurement time $t_M$. Further, if the two photodetector 41, 42 perform measurement of number of photons, each level of detection signal $M_1$, $M_2$ is proportional to a number of photons of the measuring light $P_0$ at each measurement time $t_M$.

The optical pathlength arithmetic unit 51 disposed in the arithmetic processing unit 50 calculates the mean optical pathlengths $<L(\rho_1)>$, $<L(\rho_2)>$ corresponding to the wavelengths $\lambda_1$, $\lambda_2$, $\lambda_3$ of the measuring light $P_0$ and the incidence-detection distances $\rho_1$, $\rho_2$, using Eq. (26) or Eq. (27) as being a simplified form of Eq. (8), based on the detection signals $M_1$, $M_2$ input thereinto at each sampling timing from the two photodetectors 41, 42, and outputs them to the light diffusion arithmetic unit 52.

The light diffusion arithmetic unit 52 sequentially substitutes the calculation values of mean 0optical pathlengths $<L(\rho_1)>$, $<L(\rho_2)>$, calculated by the optical pathlength arithmetic unit 51, into Eq. (9), solves Eqs. (10), (11) as simultaneous equations to calculate the absorption coefficients $\mu_A(\lambda_1)$, $\mu_A(\lambda_2)$, $\mu_A(\lambda_3)$ and transport scattering coefficients $\mu_A(\lambda_1)$, $\mu_{TS}(\lambda_2)$, $\mu_{TS}(\lambda_3)$, and then outputs them to the light absorption arithmetic unit 53.

The light absorption arithmetic unit 53 sequentially substitutes the calculation values of absorption coefficients $\mu_A(\lambda_1)$, $\mu_A(\lambda_2)$, $\mu_A(\lambda_3)$ and transport scattering coefficients $\mu_{TS}(\lambda_1)$, $\mu_{TS}(\lambda_2)$, $\mu_{TS}(\lambda_3)$ calculated by the light diffusion arithmetic unit 52, into Eq. (19) to obtain Eqs. (20) to (22), and substitutes them into Eq. (25) to obtain the hemoglobin oxygen saturation Y. Solving Eqs. (20) to (22) as simultaneous equations, the light absorption arithmetic unit 53 calculates the concentrations [Hb], [$HbO_2$] of deoxygenated hemoglobin Hb and oxygenated hemoglobin $HbO_2$ being two different absorptive constituents and outputs them with the hemoglobin oxygen saturation Y as data signals $D_0$ to the display record unit 60.

The display record unit 60 performs display or record as to the absorption coefficients $\mu_A(\lambda_1)$, $\mu_A(\lambda_2)$, $\mu_A(\lambda_3)$ and transport scattering coefficients $\mu_{TS}(\lambda_1)$, $\mu_{TS}(\lambda_2)$, $\mu_{TS}(\lambda_3)$, the concentrations [Hb], [$HbO_2$] of deoxygenated hemoglobin Hb and oxygenated hemoglobin $HbO_2$, and the hemoglobin oxygen saturation Y, coming from the light absorption arithmetic unit 53.

If such measurement is carried out at different times, the apparatus can monitor time changes of the absorption coefficients $\mu_A(\lambda_1)$, $\mu_A(\lambda_2)$, $\mu_A(\lambda_3)$ and transport scattering coefficients $\mu_{TS}(\lambda_1)$, $\mu_{TS}(\lambda_2)$, $\mu_{TS}(\lambda_3)$, the concentrations [Hb], [$HbO_2$] of deoxygenated hemoglobin Hb and oxygenated hemoglobin $HbO_2$, and the oxygen saturation Y.

In the present embodiment, a measured object is hemoglobin in the human brain. However, the measured object can be hemoglobin in a leg muscle of a man in marathon, also achieving the same operational effect as in the present embodiment.

(2.3) Third embodiment

The present embodiment is a measuring apparatus for monitoring the concentration and oxygen saturation of a measured object of hemoglobin, as applying a human mamma as a slab scattering medium and an absorptive constituent of hemoglobin in the mamma as a measured object.

Figure 11:
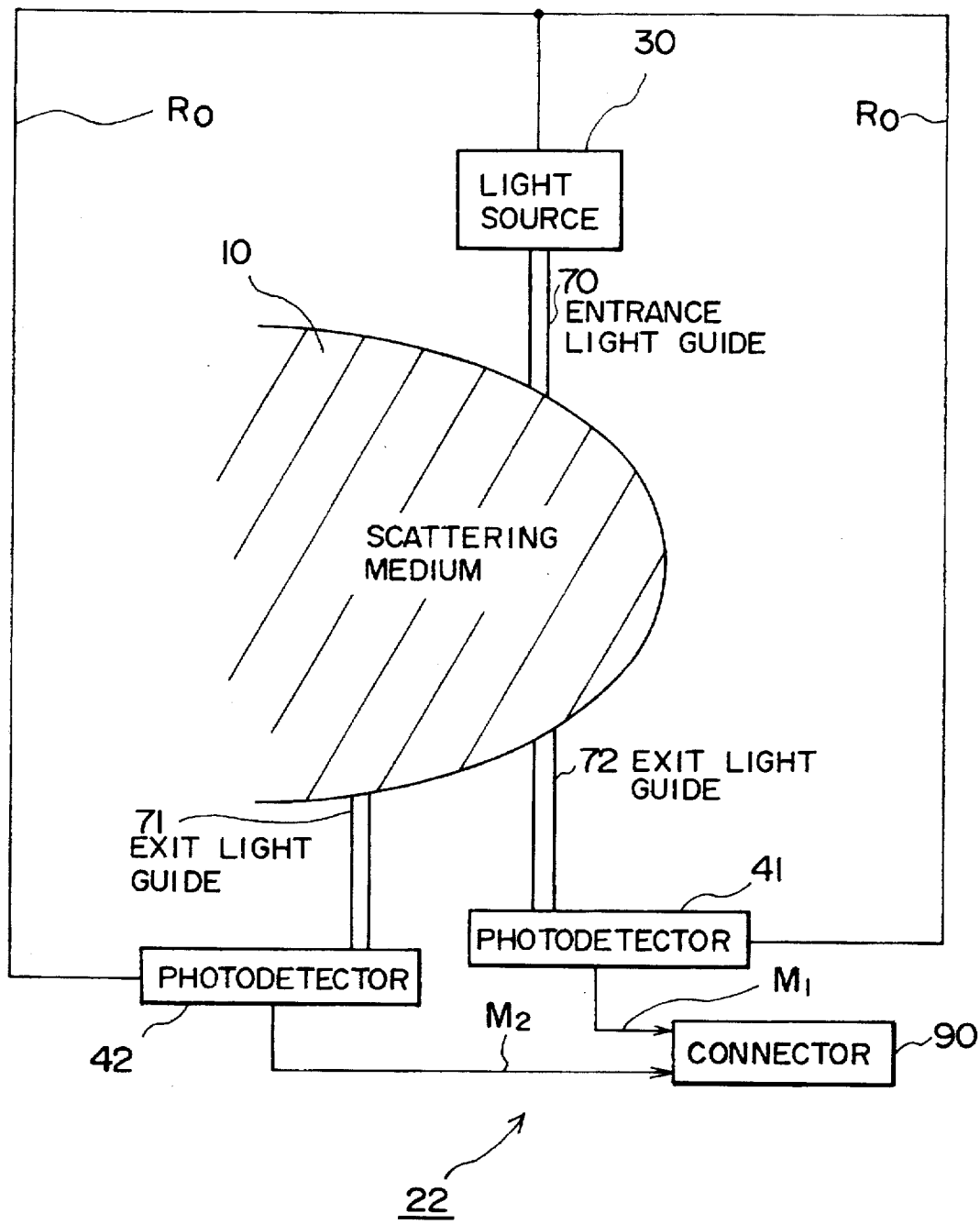
FIG. 11 is a sectional view to diagrammatically show the major part of an apparatus for measuring the scattering property and absorption property in a human mamma.

As shown in FIG. 11, the measuring apparatus 22 is constructed in the same manner as the above first embodiment. The entrance light guide 70 and two exit light guides 71, 72 are fixed on the surface of the scattering medium 10, which is a human mamma. Thicknesses of the scattering medium 10 are set to be different from each other between the entrance light guide 70 and the two exit light guides 71, 72. The connector 90 is provided between the two photodetectors 41, 42 and the signal processing system (not shown), similarly as in the above second embodiment.

The scattering medium 10 is a human mamma which contains deoxygenated hemoglobin Hb and oxygenated hemoglobin $HbO_2$ as absorptive constituents. The light source 30 emits pulsed light having three different wavelengths $\lambda_1, \lambda_2, k_3$ as measuring light $P_0$ to the two types of absorptive constituents in the scattering medium 10. The wavelengths $\lambda_1, \lambda_2, \lambda_3$ of the measuring light $P_0$ need to be set in the same manner as in the above second embodiment.

The operation of the present embodiment is next explained.

In the measuring apparatus 22 arranged in the above structure, display or record is carried out substantially in the same manner as in the above second embodiment while measuring the absorption coefficients $\mu_A(\lambda_1), \mu_A(\lambda_2), \mu_A(\lambda_3)$ and transport scattering coefficients $\mu_{TS}(\lambda_1), \mu_{TS}(\lambda_2), \mu_{TS}(\lambda_3)$, the concentrations [Hb], [$HbO_2$] of deoxygenated hemoglobin Hb and oxygenated hemoglobin $HbO_2$, and the oxygen saturation Y.

Here, the light diffusion arithmetic unit 52 sequentially substitutes the calculation values of mean optical pathlengths $<L(\rho_1)>, <L(\rho_2)>$ calculated by the optical pathlength arithmetic unit 51 into an equation equivalent to Eq. (9) obtained by substituting Eq. (12) into Eq. (8), solves equations equivalent to Eqs. (10), (11) as simultaneous equations to calculate the absorption coefficients $\mu_A(\lambda_1), \mu_A(\lambda_2), \mu_A(\lambda_3)$ and transport scattering coefficients $\mu_{TS}(\lambda_1), \mu_{TS}(\lambda_2), \mu_{TS}(\lambda_3)$, and then outputs them to the light absorption arithmetic unit 53.

If such measurement is carried out at different times, the apparatus can monitor time changes of the absorption coefficients $\mu_A(\lambda_1), \mu_A(\lambda_2), \mu_A(\lambda_3)$ and transport scattering coefficients $\mu_{TS}(\lambda_1), \mu_{TS}(\lambda_2), \mu_{TS}(\lambda_3)$, the concentrations [Hb], [$HbO_2$] of deoxygenated hemoglobin Hb and oxygenated hemoglobin $HbO_2$, and the oxygen saturation Y.

(2.4) Fourth embodiment

The present embodiment applies a human mamma as a slab scattering medium and is a measuring apparatus for imaging spatial distributions or performing easy imaging as to absorption coefficients and scattering coefficients in the mamma, and the concentration and oxygen saturation of hemoglobin as an absorptive constituent.

As shown in FIG. 12, the measuring apparatus 23 is constructed in the same manner as the above first embodiment. However, the entrance light guide 70 and two exit light guides 71, 72 are fixed on the surface of the scattering medium 10 as being a human mamma. Thicknesses of the scattering medium 10 are set to be different between the entrance light guide 70 and the two exit light guides 71, 72.

One end of a rod support 120 is fixed to an external fixing device (not shown). A drive unit 110 arranged to rotate around the support 120 is set to the other end of the support 120. One end of each rod support 121, 122 curved in a nearly L-shape is fixed to the drive unit 110 so as to project perpendicularly to the support 120 and in parallel with the other.

Two drive units 111, 112 moving along the two supports 121, 122 are arranged at the other ends of the two supports 121, 122, respectively, extending in parallel with the support 120. One ends of the entrance light guide 70 and two exit light guides 71, 72 are arranged in these two drive units 111, 112 so as to project perpendicularly to the support 120. The drive unit 112 holds the two exit light guides 71, 72 at a constant spacing.

These three drive units 110–112 are operated based on control signals $C_1, C_2, C_3$ input thereinto from a position control unit 100 to scan the entire surface of the scattering medium 10 with the entrance light guide 70 being kept as opposed to the two exit light guides 71, 72. Rotating around the support 120, the drive unit 110 rotates the entrance light guide 70 and the two exit light guides 71, 72 in the opposed state perpendicularly to the axial direction of the scattering medium 10. The two drive units 111, 112 move along the two supports 121, 122, respectively, to move the entrance light guide 70 and two exit light guides 71, 72 in the opposed state in parallel to the axial direction of the scattering medium 10. By moving the entrance light guide 70 and two exit light guides 71, 72, the one ends of the entrance light guides 70 and two exit light guides 71, 72 come into contact with the surface of scattering medium 10.

The position control unit 100 outputs the control signals $C_1, C_2, C_3$ to the three drive units 110–112 to control the scan of the entrance light guide 70 and two exit light guides 71, 72, and outputs a control signal $C_4$ to the light source 30 to generate the measuring light $P_0$ in synchronization with the scan of the entrance light guide 70 and two exit light guides 71, 72. Thus, the light source 30 emits the measuring light $P_0$ synchronized with the scan of the entrance light guide 70 and two exit light guides 71, 72, based on the control signal $C_4$ coming from the position control unit 100.

The scattering medium 10 is a human mamma, which contains deoxygenated hemoglobin Hb and oxygenated hemoglobin $HbO_2$ as absorptive constituents. The light source 30 emits the pulsed light having three different wavelengths $\lambda_1, \lambda_2, \lambda_3$ set in the same manner as in the above third embodiment as measuring light $P_0$ to the two types of absorptive constituents in the scattering medium 10.

The operation of the present embodiment is next explained.

In the measuring apparatus 23 arranged in the above structure, display or record is carried out as measuring the absorption coefficients $\mu_A(\lambda_1), \mu_A(\lambda_2), \mu_A(\lambda_3)$ and transport scattering coefficients $\mu_{TS}(\lambda_1), \mu_{TS}(\lambda_2), \mu_{TS}(\lambda_3)$, the concentrations [Hb], [$HbO_2$] of deoxygenated hemoglobin Hb and oxygenated hemoglobin $HbO_2$, and the hemoglobin oxygen saturation Y substantially in the same manner as in the above third embodiment.

Here, if such measurement is sequentially repeated as scanning the entire surface of the scattering medium 10 with the entrance light guide 70 being opposed to the two exit light guides 71, 72, based on the control of the three drive units 110–112 by the position control unit 100, spatial distributions can be imaged as to the absorption coefficients $\mu_A(\lambda_1), \mu_A(\lambda_2), \mu_A(\lambda_3)$ and transport scattering coefficients $\mu_{TS}(\lambda_1), \mu_{TS}(\lambda_2), \mu_{TS}(\lambda_3)$, the concentrations [Hb], [$HbO_2$] of deoxygenated hemoglobin Hb and oxygenated hemoglobin $HbO_2$, and the hemoglobin oxygen saturation Y.

The present invention is not intended to be limited to the above embodiments, but can include a variety of changes and modifications.

For example, in the above embodiments, (N+1) different wavelengths are set for the measuring light, corresponding to the number N of types of the absorptive constituents contained in the scattering medium. However, if the background absorption can be ignored inside the scattering medium, the same operational effect as in the above embodiments can be achieved by setting a number of wavelengths coincident with a number of types of absorptive constituents contained in the scattering medium, for the measuring light.

The above embodiments are arranged with one light source and two photodetectors. However, the same operational effect as in the above embodiments can be achieved by an arrangement using two light sources and one photodetector. Namely, it is sufficient that two different incidence-detection distances can be set for a scattering medium.

Particularly, the measurement accuracy can be improved by measuring mean optical pathlengths corresponding to many mutually different incidence-detection distances.

As detailed above, the method and apparatus for measuring the scattering property and absorption property in the scattering medium according to the present invention measure the pulsed measuring light, having diffusively propagated inside the scattering medium as being affected by scattering and absorption, in a non-invasive manner outside the scattering medium, and arithmetic-process the measurement results to calculate the scattering property and absorption property in the scattering medium. In this case, the scattering coefficient and absorption coefficient in the scattering medium are measured based on mean optical pathlengths measured for two or more different incidence-detection distances, utilizing the fact that the mean optical pathlength of measuring light depends upon light diffusion properties including the scattering property and absorption property in a diffusive propagation path inside the scattering medium.

Here, if the measuring light is set with different wavelengths in a number equal to or more than a number of types of absorptive constituents, which have different absorption coefficients for the absorptive constituents contained in the scattering medium, the concentrations of absorptive constituents can be measured based on the absorption coefficients measured for the different wavelengths: utilizing the fact that the absorption coefficient in the scattering medium for each wavelength depends upon light attenuation characteristics including contribution of each absorptive constituent in the diffusive propagation path in the scattering medium.

Thus, the mean optical pathlength of the measuring light can be measured with good accuracy as decreasing noise, because it is obtained by time quadrature of the result of time-resolved measurement of the measuring light. Further, the scattering coefficient and absorption coefficient in the scattering medium can be calculated with good accuracy based on sufficient analysis, because they can be obtained by theoretical equations derived based on the light diffusion properties including the scattering property and absorption property in the diffusive propagation path inside the scattering medium.

Accordingly, based on the theoretically and experimentally sufficient analysis for the process of the light diffusively propagating inside the scattering medium, the measurement accuracy can be improved as remarkably reducing the measurement errors as compared with the conventional methods and apparatus. For example, if the scattering medium is a living tissue and if information on the shape thereof is obtained, it becomes possible to determine whether the living tissue is a normal tissue or a tissue with a certain disorder.

If such measurement is carried out at different times and at the same light entrance position and light detection position, time changes of these quantified values can be measured. Further, if such measurement is carried out as changing the light incidence position and light detection position, spatial distributions of these quantified values can be measured.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No.272508/1994 filed on Nov. 7, 1994 is hereby incorporated by reference.

What is claimed is:

1. A method for measuring a scattering property and an absorption property in a scattering medium, comprising:

a first step of transmitting pulsed measuring light generated by a light source and having a predetermined wavelength into a scattering medium using an entrance light guide;

a second step of detecting, by a photodetector, either of light intensity or number of photons at every measuring time in said measuring light having diffusively propagated in said scattering medium at light detection positions corresponding to a plurality of combinations, each comprising a light incidence position on said scattering medium where said measuring light entered said scattering medium and a light detection position on said scattering medium where said measuring light is detected, having different incidence-detection distances between the light incidence position and the light detection position, according to a time-resolved management;

a third step of calculating a plurality of mean optical pathlengths of said measuring light corresponding to said plurality of incidence-detection distances, based on results of said time-resolved measurement measured in said second step; and a fourth step of calculating a scattering coefficient and an absorption coefficient in said scattering medium, based on a plurality of simultaneous relations consisting of calculation values of said plurality of mean optical pathlengths corresponding to said plurality of incidence-detection distances, calculated in said third step, and a theoretical equation of said mean optical pathlength derived in correspondence to light diffusion properties comprising a scattering property and an absorption property in diffusive propagation paths inside said scattering medium.

2. A method for measuring a scattering property and an absorption property in a scattering medium according to claim 1, wherein said first step comprises generating said measuring light in a pulsed form at frequency f, and said second step comprises sequentially selecting reference times $t_B = t_0 + (M-1)/f$ after said measuring light is generated by a predetermined number M of repetitions from a predetermined time $t_0$, as oscillation timings of said measuring light in said first step, sequentially setting measuring times $t_M = t_B + M \cdot \Delta t$ delayed in units of a predetermined time $\Delta t$ from said reference times $t_B$ as sampling timings of said measuring light, and thereby sequentially measuring light intensities $I(\rho, t_M)$ of said measuring light corresponding to the plurality of different said incidence-detection distances $\rho$ at every said measuring time $t_M$.

3. A method for measuring a scattering property and an absorption property in a scattering medium according to claim 2, wherein said third step comprises calculating the plurality of mean optical pathlengths $<L(\rho)> = c \cdot \Sigma_M \{I(\rho, t_M) \cdot T_M\} / \Sigma_M I(\rho, t_M)$ of said measuring light corresponding to said plurality of different incidence-detection distances $\rho$, using the light intensities $I(\rho, t_M)$ of said measuring light measured in said second step, time differences $T_M = M \cdot \Delta t$ of said measuring times $t_M$ from said reference times $t_B$, and a velocity c of said measuring light, and wherein said fourth step comprises calculating a transport scattering coefficient $\mu_{ST}$ and an absorption coefficient $\mu_A$ in said scattering medium, by solving the plurality of simultaneous theoretical equations $<L(\rho)> = (1/z_E)(\rho^2 +$ $4z_E^2)/[1+\{(2\mu_A/z_E)(\rho^2+z_E^2)\}^{1/2}]$ of said mean optical pathlength including a variable $z_E=2/\{3(\mu_A+\mu_{ST})\}$ and corresponding to said plurality of different incidence-detection distances $\rho$, using the plurality of mean optical pathlengths $<L(\rho)>$ of said measuring light calculated in said third step.

4. A method for measuring a scattering property and an absorption property in a scattering medium according to claim 1, wherein said first step comprises generating said measuring light in a pulsed form at frequency f, and wherein said second step comprises sequentially selecting reference times $t_B=t_0+(M-1)/f$ after said measuring light is generated by a predetermined number M of repetitions from a predetermined time $t_0$, as oscillation timings of said measuring light in said first step, sequentially setting measuring times $t_M=t_B+M\cdot\Delta t$ delayed in units of a predetermined time $\Delta t$ from said reference times $t_B$ as sampling timings of said measuring light, and thereby sequentially measuring numbers of photons $n(\rho, t_M)$ of said measuring light corresponding to the plurality of different said incidence-detection distances $\rho$ at every said measuring time $t_M$.

5. A method for measuring a scattering property and an absorption property in a scattering medium according to claim 4, wherein said third step comprises calculating the plurality of mean optical pathlengths $<L(\rho)>=c\cdot\Sigma_M\{n(\rho, t_M)\cdot T_M\}/\Sigma_M n(\rho, t_M)$ of said measuring light corresponding to said plurality of different incidence-detection distances $\rho$, using the numbers of photons $n(\rho, t_M)$ of said measuring light measured in said second step, time differences $T_M=M\cdot\Delta t$ of said measuring times $t_M$ from said reference times $t_B$, and a velocity c of said measuring light, and wherein said fourth step comprises calculating a transport scattering coefficient $\mu_{ST}$ and an absorption coefficient $\mu_A$ in said scattering medium, by solving the plurality of simultaneous theoretical equations $<L(\rho)>=(1/z_E)(\rho^2+4z_E^2)/[1+\{(2\mu_A/z_E)(\rho^2+z_E^2)\}^{1/2}]$ of said mean optical pathlengths including a variable $z_E=2/\{3(\mu_A+\mu_{ST})\}$ and corresponding to said plurality of different incidence-detection distances $\rho$, using the plurality of mean optical pathlengths $<L(\rho)>$ of said measuring light calculated in said third step.

6. A method for measuring a scattering property and an absorption property in a scattering medium according to claim 1, wherein said first step comprises setting a plurality of wavelengths having different absorption coefficients for absorptive constituents in said scattering medium and exceeding a number of types of said absorptive constituents, for said measuring light, said second step comprises performing time-resolved measurement of said measuring light for the plurality of wavelengths exceeding the number of types of said absorptive constituents, said third step comprises calculating the plurality of mean optical pathlengths of said measuring light for the plurality of wavelengths exceeding the number of types of said absorptive constituents, and said fourth step comprises calculating the plurality of absorption coefficients in said scattering medium for the plurality of wavelengths exceeding the number of types of said absorptive constituents, said method further comprising a fifth step of calculating concentrations of said absorptive constituents, based on a plurality of simultaneous relations consisting of the plurality of calculation values of the absorption coefficients in said scattering medium for the plurality of wavelengths exceeding the number of types of said absorptive constituents, calculated in said fourth step, and a theoretical equation of said absorption coefficient derived in correspondence to light attenuation properties including contribution of said absorptive constituents in diffusive propagation paths inside said scattering medium.

7. A method for measuring a scattering property and an absorption property in a scattering medium according to claim 6, wherein said fifth step comprises calculating the concentrations of said absorptive constituents, by solving the plurality of simultaneous theoretical equations of said absorption coefficients for the plurality of wavelengths exceeding the number of types of said absorptive constituents based on Beer-Lambert's law, using the plurality of absorption coefficients in said scattering medium calculated in said fourth step.

8. A method for measuring a scattering property and an absorption property in a scattering medium according to claim 7, wherein said first step comprises setting the plurality of wavelengths of said measuring light exceeding the number of types of said absorptive constituents so as to make coincident with each other background absorption terms in the plurality of simultaneous theoretical equations of said absorption coefficients.

9. A method for measuring a scattering property and an absorption property in a scattering medium according to claim 6, wherein the absorptive constituents in said scattering medium are deoxygenated hemoglobin Hb and oxygenated hemoglobin $HbO_2$ contained in the blood in a living tissue and the wavelengths of said measuring light are set in the range of about 700 nm to about 1.5 μm, said method further comprising a sixth step of calculating a hemoglobin oxygen saturation $Y=\{[HbO_2]/([Hb]+[HbO_2])\}\times 100$ in the blood, using the concentration [Hb] of deoxygenated hemoglobin Hb and the concentration $[HbO_2]$ of oxygenated hemoglobin $HbO_2$ calculated in said fifth step.

10. An apparatus for measuring a scattering property and an absorption property in a scattering medium, comprising:

a light source for generating pulsed measuring light having a predetermined wavelength;

an entrance light guide for outputting said measuring light coming from said light source into a scattering medium;

a photodetector for detecting either of light intensity or number of photons at every measuring time in said measuring light having diffusively propagated in said scattering medium at light detection positions corresponding to a plurality of combinations, each comprised of a light incidence position on said scattering medium where said measuring light was made incident thereinto by said light guide and a light detection position on said scattering medium where said measuring light is detected, having different incidence-detection distances between the light incidence position and the light detection position, according to time-resolved measurement of said measuring light;

an optical pathlength arithmetic unit for calculating a plurality of mean optical pathlengths of said measuring light corresponding to said plurality of incidence-detection distances, based on results of said time-resolved measurement measured by said photodetector; and a light diffusion arithmetic unit for calculating a scattering coefficient and an absorption coefficient in said scattering medium, based on a plurality of simultaneous relations consisting of calculation values of said plurality of mean optical pathlengths corresponding to said plurality of incidence-detection distances, calculated in said optical pathlength arithmetic unit, and a theoretical equation of said mean optical pathlength derived in correspondence to light diffusion properties comprising a scattering property and an absorption property in diffusive propagation paths inside said scattering medium.

11. An apparatus for measuring a scattering property and an absorption property in a scattering medium according to claim 10, wherein said light source is arranged to generate said measuring light in a pulsed form at frequency f, and wherein said photodetector is arranged to sequentially select reference times $t_B = t_0 + (M-1)/f$ after said measuring light is generated by a predetermined number M of repetitions from a predetermined time $t_0$, as oscillation timings of said measuring light by said light source, to sequentially set measuring times $t_M = t_B + M \cdot \Delta t$ delayed in units of a predetermined time $\Delta t$ from said reference times $t_B$ as sampling timings of said measuring light, and thereby sequentially measure light intensities $I(\rho, t_M)$ of said measuring light corresponding to the plurality of different said incidence-detection distances $\rho$ at every said measuring time $t_M$.

12. An apparatus for measuring a scattering property and an absorption property in a scattering medium according to claim 11, wherein said optical pathlength arithmetic unit calculates the plurality of mean optical pathlengths $<L(\rho)> = c \cdot \Sigma_M \{I(\rho, t_M) \cdot T_M\} / \Sigma_M I(\rho, t_M)$ of said measuring light corresponding to said plurality of different incidence-detection distances $\rho$, using the light intensities $I(\rho, t_M)$ of said measuring light measured in said photodetector, time differences $T_M = M \cdot \Delta t$ of said measuring times $t_M$ from said reference times $t_B$, and a velocity c of said measuring light, and wherein said light diffusion arithmetic unit calculates a transport scattering coefficient $\mu_{ST}$ and an absorption coefficient $\mu_A$ in said scattering medium, by solving the plurality of simultaneous theoretical equations $<L(\rho)> = (1/z_E)(\rho^2 + 4z_E^2)/[1 + \{(2\mu_A/z_E)(\rho^2 + z_E^2)\}^{1/2}]$ of said mean optical pathlengths including a variable $z_E = 2/\{3(\mu_A + \mu_{ST})\}$ and corresponding to said plurality of different incidence-detection distances $\rho$, using the plurality of mean optical pathlengths $<L(\rho)>$ of said measuring light calculated in said optical pathlength arithmetic unit.

13. An apparatus for measuring a scattering property and an absorption property in a scattering medium according to claim 10, wherein said light source is arranged to generate said measuring light in a pulsed form at frequency f, and wherein said photodetector is arranged to sequentially select reference times $t_B = t_0 + (M-1)/f$ after said measuring light is generated by a predetermined number M of repetitions from a predetermined time $t_0$, as oscillation timings of said measuring light by said light source, to sequentially set measuring times $t_M = t_B + M \cdot \Delta t$ delayed in units of a predetermined time $\Delta t$ from said reference time $t_B$ as sampling timings of said measuring light, and thereby to sequentially measure numbers of photons $n(\rho, t_M)$ of said measuring light corresponding to the plurality of different said incidence-detection distances $\rho$ at every said measuring time $t_M$.

14. An apparatus for measuring a scattering property and an absorption property in a scattering medium according to claim 13, wherein said optical pathlength arithmetic unit calculates the plurality of mean optical pathlengths $<L(\rho)> = c \cdot \Sigma_M \{n(\rho, t_M) \cdot T_M\} / \Sigma_M n(\rho, t_M)$ of said measuring light corresponding to said plurality of different incidence-detection distances $\rho$, using the numbers of photons $n(\rho, t_M)$ of said measuring light measured in said photodetector, time differences $T_M = M \cdot \Delta t$ of said measuring times $t_M$ from said reference times $t_B$, and a velocity c of said measuring light, and wherein said light diffusion arithmetic unit calculates a transport scattering coefficient $\mu_{ST}$ and an absorption coefficient $\mu_A$ in said scattering medium, by solving the plurality of simultaneous equations of theoretical equations $<L(\rho)> = (1/z_E)(\rho^2 + 4z_E^2)/[1 + \{(2\mu_A/z_E)(\rho^2 + z_E^2)\}^{1/2}]$ of said mean optical pathlengths including a variable $z_E = 2/\{3(\mu_A + \mu_{ST})\}$ and corresponding to said plurality of different incidence-detection distances $\rho$, using the plurality of mean optical pathlengths $<L(\rho)>$ of said measuring light calculated in said optical pathlength arithmetic unit.

15. An apparatus for measuring a scattering property and an absorption property in a scattering medium according to claim 10, wherein said light source has a wavelength controlling means for setting a plurality of wavelengths having different absorption coefficients for absorptive constituents in said scattering medium and exceeding a number of types of said absorptive constituents, for said measuring light, said photodetector performs time-resolved measurement of said measuring light for the plurality of wavelengths exceeding said number of types of absorptive constituents, said optical pathlength arithmetic unit calculates the plurality of mean optical pathlengths of said measuring light for the plurality of wavelengths exceeding the number of types of said absorptive constituents, and said light diffusion arithmetic unit calculates the plurality of absorption coefficients in said scattering medium for the plurality of wavelengths exceeding the number of types of said absorptive constituents, said apparatus further comprising a light absorption arithmetic unit for calculating concentrations of said absorptive constituents, based on a plurality of simultaneous relations consisting of the plurality of calculation values of the absorption coefficients in said scattering medium for the plurality of wavelengths exceeding the number of types of said absorptive constituents, calculated in said light diffusion arithmetic unit, and a theoretical equation of said absorption coefficient derived in correspondence to light attenuation properties including contribution of said absorptive constituents in diffusive propagation paths inside said scattering medium.

16. An apparatus for measuring a scattering property and an absorption property in a scattering medium according to claim 15, wherein said light absorption arithmetic unit calculates the concentrations of said absorptive constituents, by solving the plurality of simultaneous theoretical equations of said absorption coefficients for the plurality of wavelengths exceeding the number of types of said absorptive constituents based on Beer-Lambert's law, using the plurality of absorption coefficients in said scattering medium calculated in said light diffusion arithmetic unit.

17. An apparatus for measuring a scattering property and an absorption property in a scattering medium according to claim 16, wherein said light source sets the plurality of wavelengths of said measuring light exceeding the number of types of said absorptive constituents so as to make coincident with each other background absorption terms in the plurality of simultaneous theoretical equations of said absorption coefficients.

18. An apparatus for measuring a scattering property and an absorption property in a scattering medium according to claim 15, wherein the absorptive constituents in said scattering medium are deoxygenated hemoglobin Hb and oxygenated hemoglobin $HbO_2$ contained in the blood in a living tissue, the wavelengths of said measuring light are set in the range of about 700 nm to about 1.5 µm, and said light absorption arithmetic unit calculates a hemoglobin oxygen saturation $Y=\{[HbO_2]/([Hb]+[HbO_2])\}\times 100$ in the blood, using the concentration [Hb] of deoxygenated hemoglobin Hb and the concentration $[HbO_2]$ of oxygenated hemoglobin $HbO_2$ calculated in said light absorption arithmetic unit.

19. An apparatus for measuring a scattering property and an absorption property in a scattering medium according to claim 10, further comprising an exit light guide for taking said measuring light having diffusively propagated in said scattering medium.

20. An apparatus for measuring a scattering property and an absorption property in a scattering medium according to claim 19, further comprising an interface member disposed between said entrance light guide or said exit light guide and a surface of said scattering medium, having a refractive index and a scattering coefficient close to those of said scattering medium.

* * * * *